US012559569B2

(12) United States Patent
Lenting et al.

(10) Patent No.: US 12,559,569 B2
(45) Date of Patent: Feb. 24, 2026

(54) METHODS OF TREATING BLEEDING DISORDERS BY ADMINISTRATION OF CHIMERAS COMPRISING ANTI-VON WILLEBRAND FACTOR ANTIBODIES AND CLOTTING FACTORS

(71) Applicants: INSERM (INSTITUT NATIONAL DE LA SANTE ET DE LA RECHERCHE MEDICALE), Paris (FR); UNIVERSITE PARIS-SACLAY, Saint Aubin (FR)

(72) Inventors: Petrus Lenting, Kremlin-Bicetre (FR); Gabriel Ayme, Le Kremlin Bicetre (FR); Cecile Denis, Le Kremlin-Bicetre (FR); Olivier Christophe, Le Kremlin-Bicetre (FR)

(73) Assignees: INSERM (INSTITUT NATIONAL DE LA SANTE ET DE LA RECHERCHE MEDICALE), Paris (FR); UNIVERSITE PARIS-SACLAY, St. Aubin (FR)

( * ) Notice: Subject to any disclaimer, the term of this patent is extended or adjusted under 35 U.S.C. 154(b) by 492 days.

(21) Appl. No.: 18/068,694

(22) Filed: Dec. 20, 2022

(65) Prior Publication Data

US 2023/0203195 A1     Jun. 29, 2023

Related U.S. Application Data

(62) Division of application No. 16/818,463, filed on Mar. 13, 2020, now Pat. No. 11,560,436, which is a division of application No. 16/072,784, filed as application No. PCT/EP2017/051569 on Jan. 25, 2017, now Pat. No. 10,626,186.

(30) Foreign Application Priority Data

Jan. 26, 2016     (EP) ..................................... 16305071

(51) Int. Cl.
| | |
|---|---|
| C07K 16/36 | (2006.01) |
| A61K 39/00 | (2006.01) |
| A61P 7/04 | (2006.01) |
| C07K 14/745 | (2006.01) |
| C07K 14/755 | (2006.01) |
| C12N 15/62 | (2006.01) |

(52) U.S. Cl.
CPC ................ *C07K 16/36* (2013.01); *A61P 7/04* (2018.01); *C07K 14/745* (2013.01); *C07K 14/755* (2013.01); *C12N 15/62* (2013.01); *A61K 2039/505* (2013.01); *C07K 2317/33* (2013.01); *C07K 2317/565* (2013.01); *C07K 2317/569* (2013.01); *C07K 2317/92* (2013.01); *C07K 2317/94* (2013.01); *C07K 2319/31* (2013.01)

(58) Field of Classification Search
CPC ...... C07K 16/36; C07K 14/75; C07K 14/745; C07K 14/755; C07K 2317/94; C07K 2319/31; A61P 7/04
See application file for complete search history.

*Primary Examiner* — Elly-Gerald Stoica
(74) *Attorney, Agent, or Firm* — WCF IP

(57)     ABSTRACT

The invention relates to isolated single-domain antibodies (sdAb) directed against von Willebrand Factor (VWF) D'D3 domain and chimeric polypeptides comprising thereof such as blood clotting factors and their uses in therapy such as in the prevention and treatment of hemostatic disorders. The invention also relates to a method of extending or increasing half-life of a therapeutic polypeptide comprising a step of adding to the polypeptide sequence of said therapeutic polypeptide at least one sdAb directed against VWF D'D3 domain.

10 Claims, 5 Drawing Sheets

Figure 1:
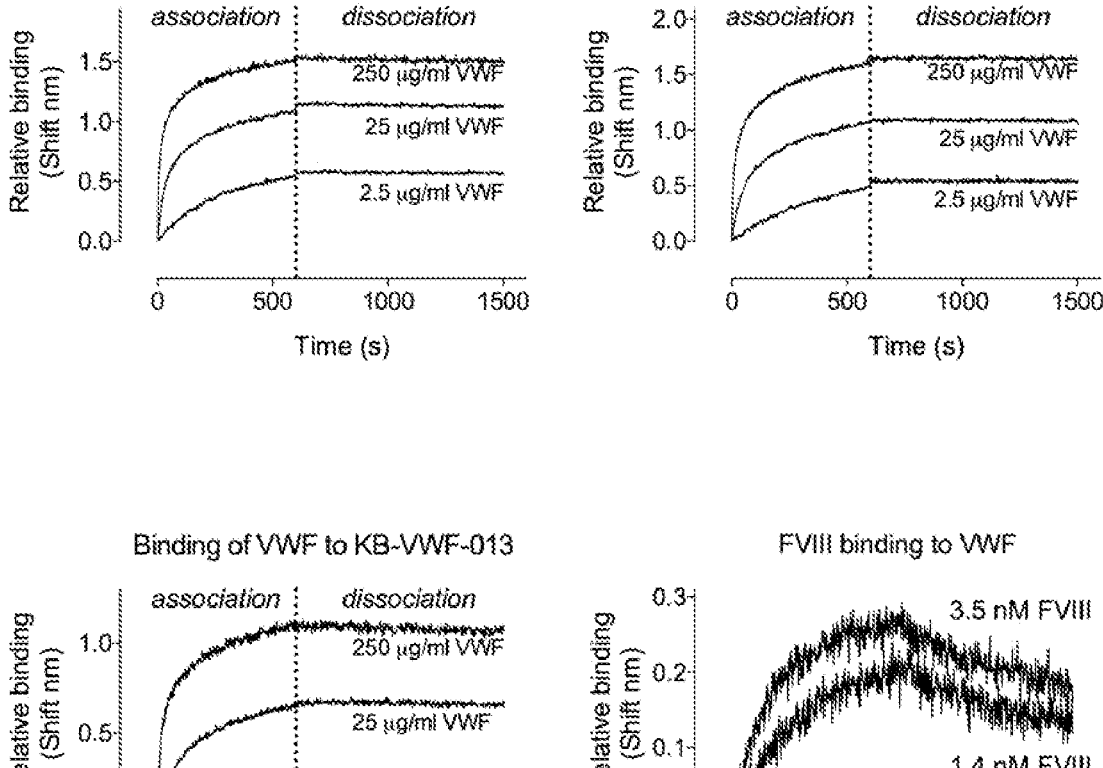

Specification includes a Sequence Listing.

| Lane | Content |
|------|---------|
| Mw | Molecular-weight-marker |
| 1 | FVIII-KB013 bv |
| 2 | FVIII-KB013 bv-after thrombin (10-nM)-incubation-30-min-room-temperature |
| 3 | WT-FVIII-SQ |
| 4 | WT-FVIII-SQ-after thrombin (10-nM)-incubation-30-min-room-temperature |

*: p=0.029 analyzed in Mann-Whitney test

METHODS OF TREATING BLEEDING DISORDERS BY ADMINISTRATION OF CHIMERAS COMPRISING ANTI-VON WILLEBRAND FACTOR ANTIBODIES AND CLOTTING FACTORS

RELATED APPLICATIONS

This application is a divisional of U.S. patent application Ser. No. 16/818,463, filed Mar. 13, 2020 (now U.S. Pat. No. 11,560,436), which is a divisional of U.S. patent application Ser. No. 16/072,784, filed Jul. 25, 2028 (now U.S. Pat. No. 10,626,186), which is the national phase of International Patent Application No. PCT/EP2017/051569, filed Jan. 25, 2027, which claims the benefit of priority to European Patent Application No. 16305071.9, filed Jan. 26, 2016, each of which is hereby incorporated by reference in its entirety.

FIELD OF THE INVENTION

The invention is in the field of immunotherapy. More particularly, the invention relates to isolated single-domain antibodies (sdAb) directed against von Willebrand Factor (VWF) D'D3 domain and polypeptides comprising thereof such as blood clotting factors and their uses in therapy such as in the prevention and treatment of hemostatic disorders.

BACKGROUND OF THE INVENTION

Extending in vivo half-life of therapeutic proteins, thereby enhancing their efficiency is a major concern in the pharmaceutical field. Numerous strategies have been employed towards this end, including covalent modification, such as through PEGylation or Fc-Fusion proteins, which improves protein stability and solubility, prevents proteolytic degradation, and reduces the clearance rate from the bloodstream. Such approaches have been applied to different therapeutic proteins and for different disorders such as Haemophilia A which is a bleeding disorder caused by defects in the gene encoding coagulation factor VIII (FVIII) and affects 1-2 in 10,000 male births. Patients affected with hemophilia A can be treated with infusion of purified plasma-derived or recombinantly produced FVIII. All commercially available FVIII products, however, are known to have a short half-life of several hours (7-21 hours, Van Dijk et al Haematologica 2005 92:494-498), requiring frequent intravenous administration to the patients. Thus, a number of approaches have been tried in order to extend the FVIII half-life. For example, the approaches in development to extend the half-life of clotting factors include chemical (PEGylation)[1] or genetic modification (Fc-fusion)[2] of the FVIII molecule. Regardless of the protein engineering used, however, the long acting FVIII products currently under development are reported to have limited half-lives—only to about 1.5 to 2 hours in preclinical animal models. Consistent results have been demonstrated in humans, for example, rFVIIIFc was reported to improve half-life up to 1.7 fold compared with ADVATE® in hemophilia A patients.

Due to the frequent dosing and inconvenience caused by the dosing schedule, there is still a need to develop FVIII products requiring less frequent administration, i.e., a FVIII product that has a half-life longer than the 1.5 to 2 fold half-life limitation.

SUMMARY OF THE INVENTION

The invention relates to isolated single-domain antibodies (sdAb) directed against von Willebrand Factor (VWF) D'D3 domain and polypeptides comprising thereof such as blood clotting factors and their uses in therapy such as in the prevention and treatment of hemostatic disorders. In particular, the present invention is defined by the claims.

DETAILED DESCRIPTION OF THE INVENTION

The invention relies on the discovery that introducing an isolated single-domain antibody (sdAb) directed against the von Willebrand factor (VWF) D'D3 domain into a therapeutic peptide leads to obtain a polypeptide with a half-life significantly increased. Indeed, the chimeric polypeptide according to the invention shows a reduced dissociation from VWF leading to more stable complex formation. This results in reduced clearance rates and thus an extended half-life. For instance, the inventors show that a chimeric FVIII polypeptide in which two isolated sdAb directed against VWF D'D3 domain (FVIII-KB013bv) are inserted thereby replacing the B-domain exhibits an extended half-life comparatively to wild-type B-domainless FVIII (T1/2 for wt-FVIII is 1.10 h (95% confidence interval: 0.88-1.48 h) and T1/2 for FVIII-KB-013bv is 2.11 h (95% CI: 1.66-2.92 h) when determined in haemophilic mice. Half-life extension is thus 2.11/1.10=1.9-fold. The sdAb directed against VWF D'D3 domain can also be used to induce complex formation with proteins that otherwise do not bind VWF. For example, a fusion protein FVII-KB013bv (consisting of FVII and two isolated sdAbs at the C-terminal end of FVII) but not FVII was found to form a complex with VWF. Furthermore, the inventors also demonstrated that such chimeric FVIII polypeptide may be complexed with VWF variants in order to improve even more its half-life (e.g. FVIII-KB013bv/D'D3-Fc). Thus, for the first time, inventors have demonstrated an increase of half-life with such construction.

Single-Domain Antibodies Directed Against VWF D'D3 Domain of the Invention:

In a first aspect, the invention relates to an isolated single-domain antibody (sdAb) directed against von Willebrand Factor (VWF) D'D3 domain By "isolated" it is meant, when referring to a single-domain antibody according to the invention, that the indicated molecule is present in the substantial absence of other biological macromolecules of the same type.

As used herein the term "single-domain antibody" (sdAb) has its general meaning in the art and refers to the single heavy chain variable domain of antibodies of the type that can be found in Camelid mammals which are naturally devoid of light chains. Such single-domain antibody are also called VHH or "Nanobody®". For a general description of (single) domain antibodies, reference is also made to the prior art cited above, as well as to EP 0 368 684, Ward et al. (Nature 1989 Oct 12; 341 (6242): 544-6), Holt et al, Trends Biotechnol, 2003, 21(11):484-490; and WO 06/030220, WO 06/003388. The amino acid sequence and structure of a single-domain antibody can be considered to be comprised of four framework regions or "FRs" which are referred to in the art and herein as "Framework region 1" or "FR1"; as "Framework region 2" or "FR2"; as "Framework region 3" or "FR3"; and as "Framework region 4" or "FR4" respectively; which framework regions are interrupted by three complementary determining regions or "CDRs", which are referred to in the art as "Complementary Determining Region 1" or "CDR1"; as "Complementarity Determining Region 2" or "CDR2" and as "Complementarity Determining Region 3" or "CDR3", respectively. Accordingly, the single-domain antibody can be defined as an amino acid sequence with the general structure: FR1-CDR1-FR2-CDR2-FR3-CDR3-FR4 in which 1-R1 to 1-R4 refer to framework regions 1 to 4 respectively, and in which CDR1 to CDR3 refer to the complementarity determining regions 1 to 3. In the context of the invention, the amino acid residues of the single-domain antibody are numbered according to the general numbering for VH domains given by the International ImMunoGeneTics information system aminoacid numbering (http://imgt.cines.fr/).

The term "VWF" has its general meaning in the art and refers to the human von Willebrand factor (VWF) which is a blood glycoprotein involved in blood clotting. VWF is a monomer composed of several homologous domains each covering different functions: D1-D2-D'-D3-A1-A2-A3-D4-C1-C2-C3-C4-C5-C6-CK. The naturally occurring human VWF protein has an aminoacid sequence as shown in GeneBank Accession number NP_000543.2. Monomers are subsequently arranged into dimers or multimers by cross-linking of cysteine residues via disulfide bonds. Multimers of VWF can thus be extremely large and can consist of over 40 monomers also called high molecular weight (HMW)-multimers of VWF.

Preferably, the single-domain antibody directed against von VWF D'D3 domain does not induce the unfolding of VWF (which leads to exposure of platelet-binding sites). Moreover, within the context of the invention the single-domain antibody directed against von VWF D'D3 domain does not block the binding to VWF of a polypeptide such as a clotting factor comprising such single-domain antibody as described below.

The inventors have isolated a single-domain antibody (sdAb) KB-VWF-013 with the required properties and characterized the complementarity determining regions (CDRs) of said KB-VWF-013 and thus determined the CDRs of said sdAb (Table A):

TABLE A

Sequences of KB-VWF-013 domains.

| KB-VWF-013 domains | Sequences |
|---|---|
| CDR1 | SEQ ID NO: 1 |
| | GRTFIRYAMA |
| CDR2 | SEQ ID NO: 2 |
| | IPQSGGRSYYADSVKG |
| CDR3 | SEQ ID NO: 3 |
| | TSTYYGRSAYSSHSGGYDY |
| SEQUENCE KB-VWF-013 | SEQ ID NO: 4 |
| | QVQLVQSGGGLVQAGDSLRLSCAAS GRTFIR |
| | YAMAWFRQAPGKEREFVAA IPQSGGRSYYAD |
| | SVKGRFTISRDNAKNTVYLQMNSLKPEDTAV |
| | YSCAATSTYYGRSAYSSHSGGYDY WGQGTQV |
| | TVSS |

In particular, the invention relates to an isolated single-domain antibody (sdAb) comprising a CDR1 having at least 80%, preferably at least 90%, more preferably at least 95%, even more preferably at least 99% sequence identity with sequence set forth as SEQ ID NO: 1, a CDR2 having at least 80%, preferably at least 90%, more preferably at least 95%, even more preferably at least 99% sequence identity with sequence set forth as SEQ ID NO: 2 and a CDR3 having at least 80%, preferably at least 90%, more preferably at least 95%, even more preferably at least 99% sequence identity with sequence set forth as SEQ ID NO: 3.

Amino acid sequence identity is preferably determined using a suitable sequence alignment algorithm and default parameters, such as BLAST P (Karlin and Altschul, Proc. Natl Acad. Sci. USA 87(6):2264-2268 (1990)).

In some embodiments, the isolated single-domain antibody according to the invention comprises a CDR1 having a sequence set forth as SEQ ID NO: 1, a CDR2 having a sequence set forth as SEQ ID NO: 2 and a CDR3 having a sequence set forth as SEQ ID NO: 3. In some embodiments, the isolated single-domain antibody according to the invention has the sequence set forth as SEQ ID NO: 4.

It should be further noted that the sdAb KB-VWF-013 cross-react with murine VWF, which is of interest for preclinical evaluation and toxicological studies.

Other examples of sdAb against VWF D'D3 that do not block FVIII binding (potential CDRs are indicated in bold):

TABLE B

Sequences of KB-VWF-008 domains.

| KB-VWF-008 domains | Sequences |
|---|---|
| CDR1 | SEQ ID NO: 5 |
| | GRTFSDYAMG |
| CDR2 | SEQ ID NO: 6 |
| | INRSGGRLSYAESVND |
| CDR3 | SEQ ID NO: 7 |
| | RTNWNPPRPLPEEYNY |
| SEQUENCE KB-VWF-008 | SEQ ID NO: 8 |
| | QVQLVQSGGGLVQAGDSLKLSCAASGRTFSDYAMGC |
| | ILQNPGKERDFVASINRSGGRLSYAESVNDLFTISV |
| | DNAKNMLYLQMNSLKPEDTAVHYCVLRTNWNPPRPL |
| | PEEYNYWGQETQVTVSS |

In particular, the invention relates to an isolated single-domain antibody (sdAb) comprising a CDR1 having at least 80%, preferably at least 90%, more preferably at least 95%, even more preferably at least 99% sequence identity with sequence set forth as SEQ ID NO: 5, a CDR2 having at least 80%, preferably at least 90%, more preferably at least 95%, even more preferably at least 99% sequence identity with sequence set forth as SEQ ID NO: 6 and a CDR3 having at least 80%, preferably at least 90%, more preferably at least 95%, even more preferably at least 99% sequence identity with sequence set forth as SEQ ID NO: 7.

In some embodiments, the isolated single-domain antibody according to the invention comprises a CDR1 having a sequence set forth as SEQ ID NO: 5, a CDR2 having a sequence set forth as SEQ ID NO: 6 and a CDR3 having a sequence set forth as SEQ ID NO: 7.

In some embodiments, the isolated single-domain antibody according to the invention has the sequence set forth as SEQ ID NO: 8.

It should be further noted that the sdAb KB-VWF-008 cross-react with canine VWF, which is of interest for preclinical evaluation and toxicological studies.

TABLE C

Sequences of KB-VWF-011 domains.

| KB-VWF-011 domains | Sequences |
|---|---|
| CDR1 | SEQ ID NO: 9<br>GGTFSNYAMG |
| CDR2 | SEQ ID NO: 10<br>ISRSGHRTDYADSAKG |
| CDR3 | SEQ ID NO: 11<br>RSDWSIATTATSYDY |
| SEQUENCE<br>KB-VWF-011 | SEQ ID NO: 12<br>QVQLVQSGGGLVQAGDSLRLSCAASGGTFSNYAMG<br>WFRQTPGKEREFVARISRSGHRTDYADSAKGRFTI<br>SRDNAKNTVYLQMNSLKPEDTAVYYCAARSDWSIA<br>TTATSYDYWGQGTQVTVSS |

In particular, the invention relates to an isolated single-domain antibody (sdAb) comprising a CDR1 having at least 80%, preferably at least 90%, more preferably at least 95%, even more preferably at least 99% sequence identity with sequence set forth as SEQ ID NO: 9, a CDR2 having at least 80%, preferably at least 90%, more preferably at least 95%, even more preferably at least 99% sequence identity with sequence set forth as SEQ ID NO: 10 and a CDR3 having at least 80%, preferably at least 90%, more preferably at least 95%, even more preferably at least 99% sequence identity with sequence set forth as SEQ ID NO: 11.

In some embodiments, the isolated single-domain antibody according to the invention comprises a CDR1 having a sequence set forth as SEQ ID NO: 9, a CDR2 having a sequence set forth as SEQ ID NO: 10 and a CDR3 having a sequence set forth as SEQ ID NO: 11.

In some embodiments, the isolated single-domain antibody according to the invention has the sequence set forth as SEQ ID NO: 12.

In some embodiments, the single domain antibody is a "humanized" single-domain antibody. As used herein the term "humanized" refers to a single-domain antibody of the invention wherein an amino acid sequence that corresponds to the amino acid sequence of a naturally occurring VHH domain has been "humanized", i.e. by replacing one or more amino acid residues in the amino acid sequence of said naturally occurring VHH sequence (and in particular in the framework sequences) by one or more of the amino acid residues that occur at the corresponding position(s) in a VH domain from a conventional chain antibody from a human being. Methods for humanizing single domain antibodies are well known in the art. Typically, the humanizing substitutions should be chosen such that the resulting humanized single domain antibodies still retain the favorable properties of single-domain antibodies of the invention. The one skilled in the art is able to determine and select suitable humanizing substitutions or suitable combinations of humanizing substitutions.

Chimeric Polypeptides of the Invention

A second aspect of the invention refers to a chimeric polypeptide comprising a polypeptide and at least one single-domain antibody directed against VWF of the invention.

As used herein, the terms "protein" or "polypeptide" refers to a polymer of two or more of the natural amino acids or non-natural amino acids.

A "fusion" or "chimeric" protein or polypeptide comprises a first amino acid sequence linked to a second amino acid sequence with which it is not naturally linked in nature. The amino acid sequences which normally exist in separate proteins can be brought together in the fusion polypeptide. A fusion protein is created, for example, by chemical synthesis, or by creating and translating a polynucleotide in which the polypeptide regions are encoded in the desired relationship. "Fusion" or "chimeric" polypeptides and proteins includes a combination of a first polypeptide chain, e.g., the FVIII protein, with a second polypeptide chain, e.g., a single-domain antibody directed against von VWF D'D3 domain In one embodiment, the chimeric polypeptide comprises any polypeptide, in particular therapeutic polypeptide, preferably having a short half-life leading to repeated administration to the patient in need thereof. Such therapeutic polypeptide may be for instance insulin, glucagon, osteoprotegerin (OPG), Angiopoietin-2 (ANGPT2) or furin.

In a particular embodiment, the chimeric polypeptide comprises a clotting factor (also referred as blood coagulation factor).

As used herein, the term "clotting factor," refers to molecules, or analogs thereof naturally occurring or recombinant produced which prevent or decrease the duration of a bleeding episode in a subject. In other words, it means molecules having pro-clotting activity, i.e., are responsible for the conversion of fibrinogen into a mesh of insoluble fibrin causing the blood to coagulate or clot. Clotting factors include factor VIII, prothrombin factors (comprising factor VII, Factor IX, factor X, protein C, protein S, protein Z and prothrombin) and clotting factor V. In a particular embodiment, the chimeric polypeptide according to the invention, wherein the polypeptide is a clotting factor selected from the group consisting of FVII, FVIII, protein C and protein S. Clotting factors of the invention may also be variants of wild-type clotting factors. The term "variants" includes insertions, deletions and substitutions, either conservative or non-conservative, where such changes do not substantially alter the active site, or active domain, which confers the biological activities of the respective clotting factor. Preferably a clotting factor is selected from the group consisting of FVII, FVIII and FX.

In one embodiment, the chimeric polypeptide comprising a polypeptide and at least one single-domain antibody directed against VWF according the invention, wherein said chimeric polypeptide has an increased affinity and/or a reduced dissociation rate constant for VWF comparatively to the wild-type polypeptide.

Without wishing to be bound by theory and knowing that affinity (i.e. affinity for VWF) is defined by $Kd=$association-rate $(k_{on})$/dissociation-rate $(k_{off})$, the chimeric polypeptide should have an increased affinity mainly due to a reduced $k_{off}$ as a result of the binding of the single-domain antibody directed against von VWF D'D3 domain to VWF.

In a preferred embodiment, the chimeric polypeptide exhibits a reduced clearance rate and thus an extended half-life when administered to a subject, compared to a corresponding polypeptide not linked to said sdAb directed against VWF and administered to said subject.

As used herein, the term "half-life" refers to a biological half-life of a particular polypeptide in vivo. Half-life may be represented by the time required for half the quantity administered to a subject to be cleared from the circulation and/or other tissues in the animal. When a clearance curve of a given polypeptide is constructed as a function of time, the curve is usually biphasic with a rapid, α-phase and longer β-phase.

Typically, the chimeric polypeptide of the invention comprises at least one single-domain antibody of the invention, which is fused at the N terminal end, at the C terminal end, or both at the N terminal end and at the C terminal end of the therapeutic polypeptide, i.e. so as to provide a fusion protein (eventually via at least one further amino acid sequence).

Alternatively, the chimeric polypeptide of the invention comprises at least one single domain antibody of the invention, which is inserted into the therapeutic polypeptide.

The term "inserted into" as used herein refers to the position of a single-domain antibody directed against von VWF D'D3 domain in a chimeric polypeptide relative to the analogous position in native polypeptide such as mature human FVIII polypeptide. The term refers to the characteristics of the chimeric polypeptide relative to native polypeptide, and do not indicate, imply or infer any methods or process by which the chimeric polypeptide was made. For example, in reference to a chimeric polypeptide provided herein, the phrase "a single-domain antibody directed against von VWF D'D3 domain is inserted downstream of residue 759 of the FVIII polypeptide" means that the chimeric polypeptide comprises a sdAb directed against von VWF D'D3 domain downstream of an amino acid which corresponds to amino acid Arg759 in native human FVIII, e.g., bounded by amino acids corresponding to amino acids Ser760 or Phe761 of native human FVIII. Importantly, to improve exposure of the sdAb in the context of the fusion protein, flexible amino acid linkers (e.g. one or multiple copies of the Gly-Gly-Gly-Ser motif) may be placed N- or C-terminally of each sdAb sequence.

As used herein, the term "insertion site" refers to a position in a polypeptide, such as a FVIII polypeptide, which is immediately upstream of the position at which a heterologous moiety can be inserted. An "insertion site" is specified as a number, the number being the number of the amino acid in said polypeptide to which the insertion site corresponds, which is immediately N-terminal to the position of the insertion.

According to the invention, the polypeptides that comprise a sole single-domain antibody are referred to herein as "monovalent" polypeptides. Polypeptides that comprise or essentially consist of two or more single-domain antibodies according to the invention are referred to herein as "multivalent" polypeptides.

The chimeric polypeptide according to the invention, comprises at least one single-domain antibody of the invention, wherein said single-domain antibody is fused at the N terminal end, at the C terminal end, both at the N terminal end and at the C terminal end of the therapeutic polypeptide or is inserted within the sequence of the therapeutic polypeptide.

In one embodiment, the polypeptide comprises two, three, four, five sdAb directed against VWF. In certain embodiments, two or more single-domain antibodies according to the invention are fused or inserted to the same terminal end or to the same insertion site.

In one embodiment, the polypeptide comprises at least one single-domain antibody of the invention and at least one other binding unit (i.e. directed against another epitope, antigen, target, protein or polypeptide), which is preferably also a single-domain antibody. Such a polypeptide is referred to herein as "multispecific" polypeptide; in opposition to a polypeptide comprising the same single-domain antibodies ("monospecific" polypeptide).

Thus, in some embodiments, the polypeptide of the invention may also provide at least one further binding site directed against any desired protein, polypeptide, antigen, antigenic determinant or epitope. Said binding site is directed against to the same protein, polypeptide, antigen, antigenic determinant or epitope for which the single domain antibody of the invention is directed again, or may be directed against a different protein, polypeptide, antigen, antigenic determinant or epitope) from the single domain antibody of the invention. A "bispecific" polypeptide of the invention is a polypeptide that comprises at least one single-domain antibody directed against a first antigen (e.g. VWF D'D3 domain) and at least one further binding site directed against a second antigen (i.e. different from VWF D'D3 domain).

In some embodiments, the further binding site is directed against a serum protein so that the half-lie of the single domain antibody is increased. Typically, said serum protein is albumin. In some embodiments, the polypeptides comprise a single domain antibody of the invention that is linked to an immunoglobulin domain For example the polypeptides comprise a single domain antibody of the invention that is linked to an Fc portion (such as a human Fc). Said Fc portion may be useful for increasing the half-life and even the production of the single domain antibody of the invention. For example the Fc portion can bind to serum proteins and thus increases the half-life on the single domain antibody.

In a particular embodiment, the clotting factor is FVIII. The terms "Factor VIII" and "FVIII" are used interchangeably herein. The FVIII protein is divided into 6 structural domains: a triplicated A domain (A1, A2, A3), a carbohydrate-rich and dispensable central domain (B-domain), and a duplicated C domain (C1, C2). In addition, the A1 and A2 domain, the A2 and B-domain and the B and A3 domain are separated by short sequences known as a1, a2 and a3, respectively, which are characterized by the presence of multiple acidic amino acids. The naturally occurring human FVIII protein has an amino acid sequence as shown in GeneBank Accession number NP_000123. "FVIII" includes wild type FVIII as well as variants of wild type FVIII having the procoagulant activity of wild type FVIII. Variants may have deletions, insertions and/or additions compared with the amino acid sequence of wild type FVIII such as mutants with reduced immunogenicity. The term FVIII includes proteolytically processed forms of FVIII. Commercially available therapeutic FVIII products include plasma derived FVIII (pdFVIII) and recombinant FVIII (rFVIII) products, such as the full-length rFVIII (Kogenate Bayer, Advate Baxter, Helixate CSL-Behring) and a B-domain deleted rFVIII (Refacto Wyeth, now marketed as Xyntha by Pfizer).

In certain embodiments, the polypeptide comprises a FVIII polypeptide and at least one sdAb directed against VWF according to the invention, wherein said FVIII polypeptide comprises A1 domain, A2 domain, A3 domain, C1 domain, C2 domain and optionally all or a portion of B domain, and wherein said at least one single-domain antibody directed against VWF is linked to said FVIII polypeptide at (i) the C-terminus of said FVIII polypeptide; (ii) within B domain of said FVIII polypeptide if all or a portion of B domain is present; (iii) within a surface loop of the A1 domain of said FVIII polypeptide; (iv) within a surface loop of the A2 domain of said FVIII polypeptide; (v) within a surface loop of the A3 domain of said FVIII polypeptide; (vi) within the C1 domain of said FVIII polypeptide; or (vii) within the C2 domain of said FVIII polypeptide; wherein said polypeptide exhibits a half-life that is extended when administered to a subject, compared to a corresponding FVIII not linked to said sdAb directed against von VWF and administered to said subject.

In one embodiment, the portion of B domain, is the portion with 1-20 amino acids of B domain (i.e. a portion comprising with the cleavage site of thrombin at position Arg740).

The typical half-life of a human FVIII in humans is several hours (7-21 hours, Van Dijk et al Haematologica 2005 92:494-498). In some embodiments, the chimeric FVIII polypeptide has extended half-life compared to wild type FVIII polypeptide. In certain embodiments, the half-life of the chimeric FVIII polypeptide is extended at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than wild type FVIII.

In a particular embodiment, two sdAb directed against VWF are inserted within the B domain of factor VIII (FVIII-KB13-bv) (SEQ ID NO: 13).

TABLE D

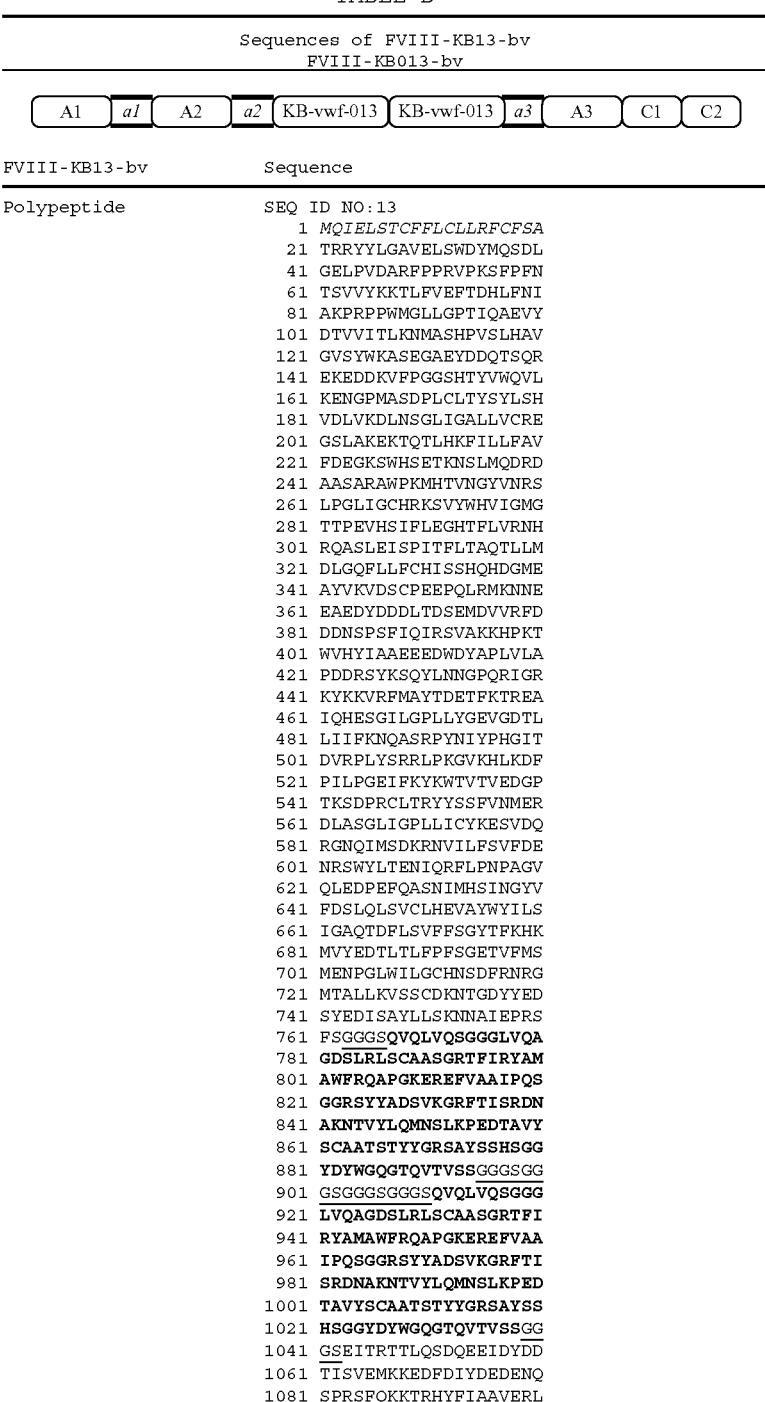

Sequences of FVIII-KB13-bv
FVIII-KB013-bv

| A1 | a1 | A2 | a2 | KB-vwf-013 | KB-vwf-013 | a3 | A3 | C1 | C2 |

| FVIII-KB13-bv | Sequence |
|---|---|
| Polypeptide | SEQ ID NO:13 |

```
   1 MQIELSTCFFLCLLRFCFSA
  21 TRRYYLGAVELSWDYMQSDL
  41 GELPVDARFPPRVPKSFPFN
  61 TSVVYKKTLFVEFTDHLFNI
  81 AKPRPPWMGLLGPTIQAEVY
 101 DTVVITLKNMASHPVSLHAV
 121 GVSYWKASEGAEYDDQTSQR
 141 EKEDDKVFPGGSHTYVWQVL
 161 KENGPMASDPLCLTYSYLSH
 181 VDLVKDLNSGLIGALLVCRE
 201 GSLAKEKTQTLHKFILLFAV
 221 FDEGKSWHSETKNSLMQDRD
 241 AASARAWPKMHTVNGYVNRS
 261 LPGLIGCHRKSVYWHVIGMG
 281 TTPEVHSIFLEGHTFLVRNH
 301 RQASLEISPITFLTAQTLLM
 321 DLGQFLLFCHISSHQHDGME
 341 AYVKVDSCPEEPQLRMKNNE
 361 EAEDYDDDLTDSEMDVVRFD
 381 DDNSPSFIQIRSVAKKHPKT
 401 WVHYIAAEEEDWDYAPLVLA
 421 PDDRSYKSQYLNNGPQRIGR
 441 KYKKVRFMAYTDETFKTREA
 461 IQHESGILGPLLYGEVGDTL
 481 LIIFKNQASRPYNIYPHGIT
 501 DVRPLYSRRLPKGVKHLKDF
 521 PILPGEIFKYKWTVTVEDGP
 541 TKSDPRCLTRYYSSFVNMER
 561 DLASGLIGPLLICYKESVDQ
 581 RGNQIMSDKRNVILFSVFDE
 601 NRSWYLTENIQRFLPNPAGV
 621 QLEDPEFQASNIMHSINGYV
 641 FDSLQLSVCLHEVAYWYILS
 661 IGAQTDFLSVFFSGYTFKHK
 681 MVYEDTLTLFPFSGETVFMS
 701 MENPGLWILGCHNSDFRNRG
 721 MTALLKVSSCDKNTGDYYED
 741 SYEDISAYLLSKNNAIEPRS
 761 FSGGGSQVQLVQSGGGLVQA
 781 GDSLRLSCAASGRTFIRYAM
 801 AWFRQAPGKEREFVAAIPQS
 821 GGRSYYADSVKGRFTISRDN
 841 AKNTVYLQMNSLKPEDTAVY
 861 SCAATSTYYGRSAYSSHSGG
 881 YDYWGQGTQVTVSSGGGSGG
 901 GSGGGSGGGSQVQLVQSGGG
 921 LVQAGDSLRLSCAASGRTFI
 941 RYAMAWFRQAPGKEREFVAA
 961 IPQSGGRSYYADSVKGRFTI
 981 SRDNAKNTVYLQMNSLKPED
1001 TAVYSCAATSTYYGRSAYSS
1021 HSGGYDYWGQGTQVTVSSGG
1041 GSEITRTTLQSDQEEIDYDD
1061 TISVEMKKEDFDIYDEDENQ
1081 SPRSFQKKTRHYFIAAVERL
```

TABLE D-continued

Sequences of FVIII-KB13-bv
FVIII-KB013-bv

| A1 | *a1* | A2 | *a2* | KB-vwf-013 | KB-vwf-013 | *a3* | A3 | C1 | C2 |

| FVIII-KB13-bv | Sequence |
|---|---|
| | 1101 WDYGMSSSPHVLRNRAQSGS |
| | 1121 VPQFKKVVFQEFTDGSFTQP |
| | 1141 LYRGELNEHLGLLGPYIRAE |
| | 1161 VEDNIMVTFRNQASRPYSFY |
| | 1181 SSLISYEEDQRQGAEPRKNF |
| | 1201 VKPNETKTYFWKVQHHMAPT |
| | 1221 KDEFDCKAWAYFSDVDLEKD |
| | 1241 VHSGLIGPLLVCHTNTLNPA |
| | 1261 HGRQVTVQEFALFFTIFDET |
| | 1281 KSWYFTENMERNCRAPCNIQ |
| | 1301 MEDPTFKENYRFHAINGYIM |
| | 1321 DTLPGLVMAQDQRIRWYLLS |
| | 1341 MGSNENIHSIHFSGHVFTVR |
| | 1361 KKEEYKMALYNLYPGVFETV |
| | 1381 EMLPSKAGIWRVECLIGEHL |
| | 1401 HAGMSTLFLVYSNKCQTPLG |
| | 1421 MASGHIRDFQITASGQYGQW |
| | 1441 APKLARLHYSGSINAWSTKE |
| | 1461 PFSWIKVDLLAPMIIHGIKT |
| | 1481 QGARQKFSSLYISQFIIMYS |
| | 1501 LDGKKWQTYRGNSTGTLMVF |
| | 1521 FGNVDSSGIKHNIFNPPIIA |
| | 1541 RYIRLHPTHYSIRSTLRMEW |
| | 1561 MGCDLNSCSMPLGMESKAIS |
| | 1581 DAQITASSYFTNMFATWSPS |
| | 1601 KARLHLQGRSNAWRPQVNNP |
| | 1621 KEWLQVDFQKTMKVTGVTTQ |
| | 1641 GVKSLLTSMYVKEFLISSSQ |
| | 1661 DGHQWTLFFQNGKVKVFQGN |
| | 1681 QDSFTPVVNSLDPPLLTRYL |
| | 1701 RIHPQSWVHQIALRMEVLGC |
| | 1721 EAQDLY* |

Italic: signal peptide, not present in the protein that circulates in plasma
Underlined: flexible linkers connecting the various elements of the fusion protein
Bold: sequence of KB-VWF-013

In a particular embodiment, two sdAb directed against VWF are inserted within the B-domain of FVIII (FVIII_KB0013bv (6GGGS)) (SEQ ID NO: 16). Linker between sdAb sequence and FVIII light chain contains 6 GGGS-sequences instead of 1.

TABLE E

Sequences of FVIII-KB13-bv (6GGGS)

| FVIII_KB0013 bv(6GGGS) | Sequence |
|---|---|
| Polypeptide | SEQ ID NO: 16<br>MQIELSTCFFLCLLRFCFSATRRYYLGAVELSWDYMQSDLGELPVD<br>ARFPPRVPKSFPFNTSVVYKKTLFVEFTDHLFNIAKPRPPWMGLLG<br>PTIQAEVYDTVVITLKNMASHPVSLHAVGVSYWKASEGAEYDDQTS<br>QREKEDDKVFPGGSHTYVWQVLKENGPMASDPLCLTYSYLSHVDLV<br>KDLNSGLIGALLVCREGSLAKEKTQTLHKFILLFAVFDEGKSWHSE<br>TKNSLMQDRDAASARAWPKMHTVNGYVNRSLPGLIGCHRKSVYWHV<br>IGMGTTPEVHSIFLEGHTFLVRNHRQASLEISPITFLTAQTLLMDL<br>GQFLLFCHISSHQHDGMEAYVKVDSCPEEPQLRMKNNEEAEDYDDD<br>LTDSEMDVVRFDDDNSPSFIQIRSVAKKHPKTWVHYIAAEEEDWDY<br>APLVLAPDDRSYKSQYLNNGPQRIGRKYKKVRFMAYTDETFKTREA<br>IQHESGILGPLLYGEVGDTLLIIFKNQASRPYNIYPHGITDVRPLY<br>SRRLPKGVKHLKDFPILPGEIFKYKWTVTVEDGPTKSDPRCLTRYY<br>SSFVNMERDLASGLIGPLLICYKESVDQRGNQIMSDKRNVILFSVF<br>DENRSWYLTENIQRFLPNPAGVQLEDPEFQASNIMHSINGYVFDSL<br>QLSVCLHEVAYWYILSIGAQTDFLSVFFSGYTFKHKMVYEDTLTLF<br>PFSGETVFMSMENPGLWILGCHNSDFRNRGMTALLKVSSCDKNTGD<br>YYEDSYEDISAYLLSKNNAIEPRSF*SGGGS*QVQLVQSGGGLVQAGD<br>SLRLSCAASGRTFIRYAMAWFRQAPGKEREFVAAIPQSGGRSYYAD<br>SVKGRFTISRDNAKNTVYLQMNSLKPEDTAVYSCAATSTYYGRSAY</sup> |

TABLE E-continued

| Sequences of FVIII-KB13-bv (6GGGS) |
| --- |

| FVIII_KB0013 bv(6GGGS) | Sequence |
| --- | --- |
| | SSHSGGYDYWGQGTQVTVSS_GGGSGGGSGGGSGGGS_QVQLVQSGGG LVQAGDSLRLSCAASGRTFIRYAMAWFRQAPGKEREFVAAIPQSGG RSYYADSVKGRFTISRDNAKNTVYLQMNSLKPEDTAVYSCAATSTY YGRSAYSSHSGGYDYWGQGTQVTVSS_GGGSGGGSGGGSGGGSGGGS_ _GGGS_EITRTTLQSDQEEIDYDDTISVEMKKEDFDIYDEDENQSPRS FQKKTRHYFIAAVERLWDYGMSSSPHVLRNRAQSGSVPQFKKVVFQ EFTDGSFTQPLYRGELNEHLGLLGPYIRAEVEDNIMVTFRNQASRP YSFYSSLISYEEDQRQGAEPRKNFVKPNETKTYFWKVQHHMAPTKD EFDCKAWAYFSDVDLEKDVHSGLIGPLLVCHTNTLNPAHGRQVTVQ EFALFFTIFDETKSWYFTENMERNCRAPCNIQMEDPTFKENYRFHA INGYIMDTLPGLVMAQDQRIRWYLLSMGSNENIHSIHFSGHVFTVR KKEEYKMALYNLYPGVFETVEMLPSKAGIWRVECLIGEHLHAGMST LFLVYSNKCQTPLGMASGHIRDFQITASGQYGQWAPKLARLHYSGS INAWSTKEPFSWIKVDLLAPMIIHGIKTQGARQKFSSLYISQFIIM YSLDGKKWQTYRGNSTGTLMVFFGNVDSSGIKHNIFNPPIIARYIR LHPTHYSIRSTLRMEWMGCDLNSCSMPLGMESKAISDAQITASSYF TNMFATWSPSKARLHLQGRSNAWRPQVNNPKEWLQVDFQKTMKVTG VTTQGVKSLLTSMYVKEFLISSSQDGHQWTLFFQNGKVKVFQGNQD SFTPVVNSLDPPLLTRYLRIHPQSWVHQIALRMEVLGCEAQDLY* |

Italic: GGGS-linker
Bold: sequence KB-VWF-013

In a particular embodiment, two sdAb directed against VWF are inserted within the B-domain of FVIII (FVIII_KB0013bv (6GGGS)_Y1680F) (SEQ ID NO: 17). Linker between sdAb sequence and FVIII light chain contains 6 GGGS-sequences instead of 1. The Y1680F mutation to avoid natural binding of FVIII to VWF (binding is only mediated by sdAb).

TABLE F

| Sequences of FVIII_KB0013bv(6GGGS)_Y1680F |
| --- |

| FVIII_KB0013bv (6GGGS)_Y1680F | Sequence |
| --- | --- |
| Polypeptide | SEQ ID NO: 17 MQIELSTCFFLCLLRFCFSATRRYYLGAVELSWDYMQSDLGELPVD ARFPPRVPKSFPFNTSVVYKKTLFVEFTDHLFNIAKPRPPWMGLLG PTIQAEVYDTVVITLKNMASHPVSLHAVGVSYWKASEGAEYDDQTS QREKEDDKVFPGGSHTYVWQVLKENGPMASDPLCLTYSYLSHVDLV KDLNSGLIGALLVCREGSLAKEKTQTLHKFILLFAVFDEGKSWHSE TKNSLMQDRDAASARAWPKMHTVNGYVNRSLPGLIGCHRKSVYWHV IGMGTTPEVHSIFLEGHTFLVRNHRQASLEISPITFLTAQTLLMDL GQFLLFCHISSHQHDGMEAYVKVDSCPEEPQLRMKNNEEAEDYDDD LTDSEMDVVRFDDDNSPSFIQIRSVAKKHPKTWVHYIAAEEEDWDY APLVLAPDDRSYKSQYLNNGPQRIGRKYKKVRFMAYTDETFKTREA IQHESGILGPLLYGEVGDTLLIIFKNQASRPYNIYPHGITDVRPLY SRRLPKGVKHLKDFPILPGEIFKYKWTVTVEDGPTKSDPRCLTRYY SSFVNMERDLASGLIGPLLICYKESVDQRGNQIMSDKRNVILFSVF DENRSWYLTENIQRFLPNPAGVQLEDPEFQASNIMHSINGYVFDSL QLSVCLHEVAYWYILSIGAQTDFLSVFFSGYTFKHKMVYEDTLTLF PFSGETVFMSMENPGLWILGCHNSDFRNRGMTALLKVSSCDKNTGD YYEDSYEDISAYLLSKNNAIEPRSF_SGGGS_QVQLVQSGGGLVQAGD SLRLSCAASGRTFIRYAMAWFRQAPGKEREFVAAIPQSGGRSYYAD SVKGRFTISRDNAKNTVYLQMNSLKPEDTAVYSCAATSTYYGRSAY SSHSGGYDYWGQGTQVTVSS_GGGSGGGSGGGSGGGS_QVQLVQSGGG LVQAGDSLRLSCAASGRTFIRYAMAWFRQAPGKEREFVAAIPQSGG RSYYADSVKGRFTISRDNAKNTVYLQMNSLKPEDTAVYSCAATSTY YGRSAYSSHSGGYDYWGQGTQVTVSS_GGGSGGGSGGGSGGGSGGGS_ _GGGS_EITRTTLQSDQEEIDYDDTISVEMKKEDFDIFDEDENQSPRS FQKKTRHYFIAAVERLWDYGMSSSPHVLRNRAQSGSVPQFKKVVFQ EFTDGSFTQPLYRGELNEHLGLLGPYIRAEVEDNIMVTFRNQASRP YSFYSSLISYEEDQRQGAEPRKNFVKPNETKTYFWKVQHHMAPTKD EFDCKAWAYFSDVDLEKDVHSGLIGPLLVCHTNTLNPAHGRQVTVQ EFALFFTIFDETKSWYFTENMERNCRAPCNIQMEDPTFKENYRFHA INGYIMDTLPGLVMAQDQRIRWYLLSMGSNENIHSIHFSGHVFTVR KKEEYKMALYNLYPGVFETVEMLPSKAGIWRVECLIGEHLHAGMST LFLVYSNKCQTPLGMASGHIRDFQITASGQYGQWAPKLARLHYSGS INAWSTKEPFSWIKVDLLAPMIIHGIKTQGARQKFSSLYISQFIIM |

TABLE F-continued

Sequences of FVIII_KB0013bv(6GGGS)_Y1680F

| FVIII_KB0013bv (6GGGS)_Y1680F | Sequence |
|---|---|
| | YSLDGKKWQTYRGNSTGTLMVFFGNVDSSGIKHNIFNPPIIARYIR LHPTHYSIRSTLRMEWMGCDLNSCSMPLGMESKAISDAQITASSYF TNMFATWSPSKARLHLQGRSNAWRPQVNNPKEWLQVDFQKTMKVTG VTTQGVKSLLTSMYVKEFLISSSQDGHQWTLFFQNGKVKVFQGNQD SFTPVVNSLDPPLLTRYLRIHPQSWVHQIALRMEVLGCEAQDLY* |

Italic: GGGS-linker
Bold: sequence KB-VWF-013
Bold underline: mutation p.Y1680F

In a particular embodiment, two sdAb directed against VWF are inserted at C terminus of FVIII (FVIII_BD_Cter-0013bv) (SEQ ID NO: 18).

TABLE G

Sequences of FVIII_BD_Cter-0013bv

| FVIII_BD_Cter-0013bv | Sequence |
|---|---|
| Polypeptide | SEQ ID NO: 18 MQIELSTCFFLCLLRFCFSATRRYYLGAVELSWDYMQSDLGELPVD ARFPPRVPKSFPFNTSVVYKKTLFVEFTDHLFNIAKPRPPWMGLLG PTIQAEVYDTVVITLKNMASHPVSLHAVGVSYWKASEGAEYDDQTS QREKEDDKVFPGGSHTYVWQVLKENGPMASDPLCLTYSYLSHVDLV KDLNSGLIGALLVCREGSLAKEKTQTLHKFILLFAVFDEGKSWHSE TKNSLMQDRDAASARAWPKMHTVNGYVNRSLPGLIGCHRKSVYWHV IGMGTTPEVHSIFLEGHTFLVRNHRQASLEISPITFLTAQTLLMDL GQFLLFCHISSHQHDGMEAYVKVDSCPEEPQLRMKNNEEAEDYDDD LTDSEMDVVRFDDDNSPSFIQIRSVAKKHPKTWVHYIAAEEEDWDY APLVLAPDDRSYKSQYLNNGPQRIGRKYKKVRFMAYTDETFKTREA IQHESGILGPLLYGEVGDTLLIIFKNQASRPYNIYPHGITDVRPLY SRRLPKGVKHLKDFPILPGEIFKYKWTVTVEDGPTKSDPRCLTRYY SSFVNMERDLASGLIGPLLICYKESVDQRGNQIMSDKRNVILFSVF DENRSWYLTENIQRFLPNPAGVQLEDPEFQASNIMHSINGYVFDSL QLSVCLHEVAYWYILSIGAQTDFLSVFFSGYTFKHKMVYEDTLTLF PFSGETVFMSMENPGLWILGCHNSDFRNRGMTALLKVSSCDKNTGD YYEDSYEDISAYLLSKNNAIEPRSFSQNPPVLKRHQREITRTTLQS DQEEIDYDDTISVEMKKEDFDIYDEDENQSPRSFQKKTRHYFIAAV ERLWDYGMSSSPHVLRNRAQSGSVPQFKKVVFQEFTDGSFTQPLYR GELNEHLGLLGPYIRAEVEDNIMVTFRNQASRPYSFYSSLISYEED QRQGAEPRKNFVKPNETKTYFWKVQHHMAPTKDEFDCKAWAYFSDV DLEKDVHSGLIGPLLVCHTNTLNPAHGRQVTVQEFALFFTIFDETK SWYFTENMERNCRAPCNIQMEDPTFKENYRFHAINGYIMDTLPGLV MAQDQRIRWYLLSMGSNENIHSIHFSGHVFTVRKKEEYKMALYNLY PGVFETVEMLPSKAGIWRVECLIGEHLHAGMSTLFLVYSNKCQTPL GMASGHIRDFQITASGQYGQWAPKLARLHYSGSINAWSTKEPFSWI KVDLLAPMIIHGIKTQGARQKFSSLYISQFIIMYSLDGKKWQTYRG NSTGTLMVFFGNVDSSGIKHNIFNPPIIARYIRLHPTHYSIRSTLR MEWMGCDLNSCSMPLGMESKAISDAQITASSYFTNMFATWSPSKAR LHLQGRSNAWRPQVNNPKEWLQVDFQKTMKVTGVTTQGVKSLLTSM YVKEFLISSSQDGHQWTLFFQNGKVKVFQGNQDSFTPVVNSLDPPL LTRYLRIHPQSWVHQIALRMEVLGCEAQDLYLTPRGVRLGGGSGGG SGGGSGGGSQVQLVQSGGGLVQAGDSLRLSCAASGRTFIRYAMAWF RQAPGKEREFVAAIPQSGGRSYYADSVKGRFTISRDNAKNTVYLQM NSLKPEDTAVYSCAATSTYYGRSAYSSHSGGYDYWGQGTQVTVSSG GGSGGGSGGGSGGGSQVQLVQSGGGLVQAGDSLRLSCAASGRTFIR YAMAWFRQAPGKEREFVAAIPQSGGRSYYADSVKGRFTISRDNAKN TVYLQMNSLKPEDTAVYSCAATSTYYGRSAYSSHSGGYDYWGQGTQ VTVSS* |

Italic: GGGS-linker
Bold: sequence KB-VWF-013
Underline: thrombin-cleavage site

In a particular embodiment, two sdAb directed against VWF are inserted at C terminus of FVIII (FVIII_BD_Cter-0013bv_Y1680F) (SEQ ID NO: 19). The Y1680F mutation to avoid natural binding of FVIII to VWF (binding is only mediated by sdAb).

TABLE H

Sequences of FVIII_BD_Cter-0013bv_Y1680F

| FVIIL_BD_Cter-0013bv_Y1680F | Sequence |
|---|---|
| Polypeptide | SEQ ID NO: 19<br>MQIELSTCFFLCLLRFCFSATRRYYLGAVELSWDYMQSDLGELP<br>VDARFPPRVPKSFPFNTSVVYKKTLFVEFTDHLFNIAKPRPPWM<br>GLLGPTIQAEVYDTVVITLKNMASHPVSLHAVGVSYWKASEGAE<br>YDDQTSQREKEDDKVFPGGSHTYVWQVLKENGPMASDPLCLTYS<br>YLSHVDLVKDLNSGLIGALLVCREGSLAKEKTQTLHKFILLFAV<br>FDEGKSWHSETKNSLMQDRDAASARAWPKMHTVNGYVNRSLPGL<br>IGCHRKSVYWHVIGMGTTPEVHSIFLEGHTFLVRNHRQASLEIS<br>PITFLTAQTLLMDLGQFLLFCHISSHQHDGMEAYVKVDSCPEEP<br>QLRMKNNEEAEDYDDDLTDSEMDVVRFDDDNSPSFIQIRSVAKK<br>HPKTWVHYIAAEEEDWDYAPLVLAPDDRSYKSQYLNNGPQRIGR<br>KYKKVRFMAYTDETFKTREAIQHESGILGPLLYGEVGDTLLIIF<br>KNQASRPYNIYPHGITDVRPLYSRRLPKGVKHLKDFPILPGEIF<br>KYKWTVTVEDGPTKSDPRCLTRYYSSFVNMERDLASGLIGPLLI<br>CYKESVDQRGNQIMSDKRNVILFSVFDENRSWYLTENIQRFLPN<br>PAGVQLEDPEFQASNIMHSINGYVFDSLQLSVCLHEVAYWYILS<br>IGAQTDFLSVFFSGYTFKHKMVYEDTLTLFPFSGETVFMSMENP<br>GLWILGCHNSDFRNRGMTALLKVSSCDKNTGDYYEDSYEDISAY<br>LLSKNNAIEPRSFSQNPPVLKRHQREITRTTLQSDQEEIDYDDT<br>ISVEMKKEDFDIFDEDENQSPRSFQKKTRHYFIAAVERLWDYGM<br>SSSPHVLRNRAQ<u>S</u>GSVPQFKKVVFQEFTDGSFTQPLYRGELNEH<br>LGLLGPYIRAEVEDNIMVTFRNQASRPYSFYSSLISYEEDQRQG<br>AEPRKNFVKPNETKTYFWKVQHHMAPTKDEFDCKAWAYFSDVDL<br>EKDVHSGLIGPLLVCHTNTLNPAHGRQVTVQEFALFFTIFDETK<br>SWYFTENMERNCRAPCNIQMEDPTFKENYRFHAINGYIMDTLPG<br>LVMAQDQRIRWYLLSMGSNENIHSIHFSGHVFTVRKKEEYKMAL<br>YNLYPGVFETVEMLPSKAGIWRVECLIGEHLHAGMSTLFLVYSN<br>KCQTPLGMASGHIRDFQITASGQYGQWAPKLARLHYSGSINAWS<br>TKEPFSWIKVDLLAPMIIHGIKTQGARQKFSSLYISQFIIMYSL<br>DGKKWQTYRGNSTGTLMVFFGNVDSSGIKHNIFNPPIIARYIRL<br>HPTHYSIRSTLRMEWMGCDLNSCSMPLGMESKAISDAQITASSY<br>FTNMFATWSPSKARLHLQGRSNAWRPQVNNPKEWLQVDFQKTMK<br>VTGVTTQGVKSLLTSMYVKEFLISSSQDGHQWTLFFQNGKVKVF<br>QGNQDSFTPVVNSLDPPLLTRYLRIHPQSWVHQIALRMEVLGCE<br>AQDLYLTPRGVRL*GGGSGGGSGGGSGGGS*QVQLVQSGGGLVQAG<br>DSLRLSCAASGRTFIRYAMAWFRQAPGKEREFVAAIPQSGGRSY<br>YADSVKGRFTISRDNAKNTVYLQMNSLKPEDTAVYSCAATSTYY<br>GRSAYSSHSGGYDYWGQGTQVTVSS_GGGSGGGSGGGSGGGS_QVQ<br>LVQSGGGLVQAGDSLRLSCAASGRTFIRYAMAWFRQAPGKEREF<br>VAAIPQSGGRSYYADSVKGRFTISRDNAKNTVYLQMNSLKPEDT<br>AVYSCAATSTYYGRSAYSSHSGGYDYWGQGTQVTVSS*** |

Italic: GGGS-linker
Bold: sequence KB-VWF-013
Underline: thrombin-cleavage site
Bold underline: mutation p.Y1680F In a particular embodiment, two sdAb directed against VWF are inserted within the B-domain of FVIII, while two sdAb are inserted at the C-terminus (FVIII_KB0013bv_Cter-0013bv) (SEQ ID NO: 20).

TABLE 1

Sequences of FVIII_KB0013bv_Cter-0013bv

| FVIII_KB0013bv_Cter-0013bv | Sequence |
|---|---|
| Polypeptide | SEQ ID NO: 20<br>MQIELSTCFFLCLLRFCFSATRRYYLGAVELSWDYMQSDLGELP<br>VDARFPPRVPKSFPFNTSVVYKKTLFVEFTDHLFNIAKPRPPWM<br>GLLGPTIQAEVYDTVVITLKNMASHPVSLHAVGVSYWKASEGAE<br>YDDQTSQREKEDDKVFPGGSHTYVWQVLKENGPMASDPLCLTYS<br>YLSHVDLVKDLNSGLIGALLVCREGSLAKEKTQTLHKFILLFAV<br>FDEGKSWHSETKNSLMQDRDAASARAWPKMHTVNGYVNRSLPGL<br>IGCHRKSVYWHVIGMGTTPEVHSIFLEGHTFLVRNHRQASLEIS<br>PITFLTAQTLLMDLGQFLLFCHISSHQHDGMEAYVKVDSCPEEP<br>QLRMKNNEEAEDYDDDLTDSEMDVVRFDDDNSPSFIQIRSVAKK<br>HPKTWVHYIAAEEEDWDYAPLVLAPDDRSYKSQYLNNGPQRIGR<br>KYKKVRFMAYTDETFKTREAIQHESGILGPLLYGEVGDTLLIIF<br>KNQASRPYNIYPHGITDVRPLYSRRLPKGVKHLKDFPILPGEIF<br>KYKWTVTVEDGPTKSDPRCLTRYYSSFVNMERDLASGLIGPLLI<br>CYKESVDQRGNQIMSDKRNVILFSVFDENRSWYLTENIQRFLPN<br>PAGVQLEDPEFQASNIMHSINGYVFDSLQLSVCLHEVAYWYILS |

TABLE 1-continued

Sequences of FVIII_KB0013bv_Cter-0013bv

FVIII_KB0013bv_Cter-
0013bv                    Sequence

IGAQTDFLSVFFSGYTFKHKMVYEDTLTLFPFSGETVFMSMENP
GLWILGCHNSDFRNRGMTALLKVSSCDKNTGDYYEDSYEDISAY
LLSKNNAIEPRSF*SGGGS*QVQLVQSGGGLVQAGDSLRLSCAASG
RTFIRYAMAWFRQAPGKEREFVAAIPQSGGRSYYADSVKGRFTI
SRDNAKNTVYLQMNSLKPEDTAVYSCAATSTYYGRSAYSSHSGG
YDYWGQGTQVTVSS*GGGSGGGSGGGSGGGS*QVQLVQSGGGLVQA
GDSLRLSCAASGRTFIRYAMAWFRQAPGKEREFVAAIPQSGGRS
YYADSVKGRFTISRDNAKNTVYLQMNSLKPEDTAVYSCAATSTY
YGRSAYSSHSGGYDYWGQGTQVTVSS*GGGS*EITRTTLQSDQEEI
DYDDTISVEMKKEDFDIYDEDENQSPRSFQKKTRHYFIAAVERL
WDYGMSSSPHVLRNRAQSGSVPQFKKVVFQEFTDGSFTQPLYRG
ELNEHLGLLGPYIRAEVEDNIMVTFRNQASRPYSFYSSLISYEE
DQRQGAEPRKNFVKPNETKTYFWKVQHHMAPTKDEFDCKAWAYF
SDVDLEKDVHSGLIGPLLVCHTNTLNPAHGRQVTVQEFALFFTI
FDETKSWYFTENMERNCRAPCNIQMEDPTFKENYRFHAINGYIM
DTLPGLVMAQDQRIRWYLLSMGSNENIHSIHFSGHVFTVRKKEE
YKMALYNLYPGVFETVEMLPSKAGIWRVECLIGEHLHAGMSTLF
LVYSNKCQTPLGMASGHIRDFQITASGQYGQWAPKLARLHYSGS
INAWSTKEPFSWIKVDLLAPMIIHGIKTQGARQKFSSLYISQFI
IMYSLDGKKWQTYRGNSTGTLMVFFGNVDSSGIKHNIFNPPIIA
RYIRLHPTHYSIRSTLRMEWMGCDLNSCSMPLGMESKAISDAQI
TASSYFTNMFATWSPSKARLHLQGRSNAWRPQVNNPKEWLQVDF
QKTMKVTGVTTQGVKSLLTSMYVKEFLISSSQDGHQWTLFFQNG
KVKVFQGNQDSFTPVVNSLDPPLLTRYLRIHPQSWVHQIALRME
VLGCEAQDLYLTPRGVRL*GGGSGGGSGGGSGGGS*QVQLVQSGGG
LVQAGDSLRLSCAASGRTFIRYAMAWFRQAPGKEREFVAAIPQS
GGRSYYADSVKGRFTISRDNAKNTVYLQMNSLKPEDTAVYSCAA
TSTYYGRSAYSSHSGGYDYWGQGTQVTVSS*GGGSGGGSGGGSGG*
*GS*QVQLVQSGGGLVQAGDSLRLSCAASGRTFIRYAMAWFRQAPG
KEREFVAAIPQSGGRSYYADSVKGRFTISRDNAKNTVYLQMNSL
KPEDTAVYSCAATSTYYGRSAYSSHSGGYDYWGQGTQVTVSS*

Italic: GGGS-linker
Bold: sequence KB-VWF-013
Underline: thrombin-cleavage site

35

In a particular embodiment, two sdAb directed against VWF are inserted within the B-domain of FVIII, while two sdAb are inserted at the C-terminus (FVIII_KB0013bv_Cter-0013bv_Y1680F) (SEQ ID NO: 21). The Y1680F mutation allows to avoid natural binding of FVIII to VWF (binding is only mediated by sdAb). C-terminal thrombin cleavage site allows to release sdAb upon FVIII activation.

TABLE J

Sequences of FVIII_KB0013bv_Cter-0013bv_Y1680F

FVIII_KB0013bvCter-
0013bv_Y1680F            Sequence

Polypeptide              SEQ ID NO: 21
                         MQIELSTCFFLCLLRFCFSATRRYYLGAVELSWDYMQSDLGELP
                         VDARFPPRVPKSFPFNTSVVYKKTLFVEFTDHLFNIAKPRPPWM
                         GLLGPTIQAEVYDTVVITLKNMASHPVSLHAVGVSYWKASEGAE
                         YDDQTSQREKEDDKVFPGGSHTYVWQVLKENGPMASDPLCLTYS
                         YLSHVDLVKDLNSGLIGALLVCREGSLAKEKTQTLHKFILLFAV
                         FDEGKSWHSETKNSLMQDRDAASARAWPKMHTVNGYVNRSLPGL
                         IGCHRKSVYWHVIGMGTTPEVHSIFLEGHTFLVRNHRQASLEIS
                         PITFLTAQTLLMDLGQFLLFCHISSHQHDGMEAYVKVDSCPEEP
                         QLRMKNNEEAEDYDDDLTDSEMDVVRFDDDNSPSFIQIRSVAKK
                         HPKTWVHYIAAEEEDWDYAPLVLAPDDRSYKSQYLNNGPQRIGR
                         KYKKVRFMAYTDETFKTREAIQHESGILGPLLYGEVGDTLLIIF
                         KNQASRPYNIYPHGITDVRPLYSRRLPKGVKHLKDFPILPGEIF
                         KYKWTVTVEDGPTKSDPRCLTRYYSSFVNMERDLASGLIGPLLI
                         CYKESVDQRGNQIMSDKRNVILFSVFDENRSWYLTENIQRFLPN
                         PAGVQLEDPEFQASNIMHSINGYVFDSLQLSVCLHEVAYWYILS
                         IGAQTDFLSVFFSGYTFKHKMVYEDTLTLFPFSGETVFMSMENP
                         GLWILGCHNSDFRNRGMTALLKVSSCDKNTGDYYEDSYEDISAY
                         LLSKNNAIEPRSF*SGGGS*QVQLVQSGGGLVQAGDSLRLSCAASG
                         RTFIRYAMAWFRQAPGKEREFVAAIPQSGGRSYYADSVKGRFTI
                         SRDNAKNTVYLQMNSLKPEDTAVYSCAATSTYYGRSAYSSHSGG
                         YDYWGQGTQVTVSS*GGGSGGGSGGGSGGGS*QVQLVQSGGGLVQA
                         GDSLRLSCAASGRTFIRYAMAWFRQAPGKEREFVAAIPQSGGRS
                         YYADSVKGRFTISRDNAKNTVYLQMNSLKPEDTAVYSCAATSTY
                         YGRSAYSSHSGGYDYWGQGTQVTVSS*GGGS*EITRTTLQSDQEEI

TABLE J-continued

Sequences of FVIII_KB0013bv_Cter-0013bv_Y1680F

| FVIII_KB0013bvCter-0013bv_Y1680F | Sequence |
|---|---|
| | DYDDTISVEMKKEDFDIFDEDENQSPRSFQKKTRHYFIAAVERL |
| | WDYGMSSSPHVLRNRAQ<u>SG</u>SVPQFKKVVFQEFTDGSFTQPLYRG |
| | ELNEHLGLLGPYIRAEVEDNIMVTFRNQASRPYSFYSSLISYEE |
| | DQRQGAEPRKNFVKPNETKTYFWKVQHHMAPTKDEFDCKAWAYF |
| | SDVDLEKDVHSGLIGPLLVCHTNTLNPAHGRQVTVQEFALFFTI |
| | FDETKSWYFTENMERNCRAPCNIQMEDPTFKENYRFHAINGYIM |
| | DTLPGLVMAQDQRIRWYLLSMGSNENIHSIHFSGHVFTVRKKEE |
| | YKMALYNLYPGVFETVEMLPSKAGIWRVECLIGEHLHAGMSTLF |
| | LVYSNKCQTPLGMASGHIRDFQITASGQYGQWAPKLARLHYSGS |
| | INAWSTKEPFSWIKVDLLAPMIIHGIKTQGARQKFSSLYISQFI |
| | IMYSLDGKKWQTYRGNSTGTLMVFFGNVDSSGIKHNIFNPPIIA |
| | RYIRLHPTHYSIRSTLRMEWMGCDLNSCSMPLGMESKAISDAQI |
| | TASSYFTNMFATWSPSKARLHLQGRSNAWRPQVNNPKEWLQVDF |
| | QKTMKVTGVTTQGVKSLLTSMYVKEFLISSSQDGHQWTLFFQNG |
| | KVKVFQGNQDSFTPVVNSLDPPLLTRYLRIHPQSWVHQIALRME |
| | VLGCEAQDLYLTPRGVRL*GGGSGGGSGGGSGGGS*QVQLVQSGGG |
| | LVQAGDSLRLSCAASGRTFIRYAMAWFRQAPGKEREFVAAIPQS |
| | GGRSYYADSVKGRFTISRDNAKNTVYLQMNSLKPEDTAVYSCAA |
| | TSTYYGRSAYSSHSGGYDYWGQGTQVTVSS*GGGSGGGSGGGSGG* |
| | *GSG*QVQLVQSGGGLVQAGDSLRLSCAASGRTFIRYAMAWFRQAPG |
| | KEREFVAAIPQSGGRSYYADSVKGRFTISRDNAKNTVYLQMNSL |
| | KPEDTAVYSCAATSTYYGRSAYSSHSGGYDYWGQGTQVTVSS\* |

*Italic: GGGS-linker*
Bold: sequence KB-VWF-013
<u>Underline: thrombin-cleavage site</u>
<u>Bold underline: mutation p.Y1680F</u>

In a particular embodiment, two sdAb directed against VWF are inserted within the B-domain of FVIII, while two sdAb are inserted at the C-terminus (FVIII_KB0013bv (6GGGS)_Cter-0013bv) (SEQ ID NO: 22). Linker between sdAb sequence and FVIII light chain contains 6 GGGS-sequences instead of 1. The C-terminal thrombin cleavage site allows to release sdAb upon FVIII activation.

TABLE K

Sequences of FVIII_KB0013bv(6GGGS)_Cter-0013bv

| FVIII_KB0013bv (6GGGS)_Cter-0013bv | Sequence |
|---|---|
| Polypeptide | SEQ ID NO: 22 |
| | MQIELSTCFFLCLLRFCFSATRRYYLGAVELSWDYMQSDLGELP |
| | VDARFPPRVPKSFPFNTSVVYKKTLFVEFTDHLFNIAKPRPPWM |
| | GLLGPTIQAEVYDTVVITLKNMASHPVSLHAVGVSYWKASEGAE |
| | YDDQTSQREKEDDKVFPGGSHTYVWQVLKENGPMASDPLCLTYS |
| | YLSHVDLVKDLNSGLIGALLVCREGSLAKEKTQTLHKFILLFAV |
| | FDEGKSWHSETKNSLMQDRDAASARAWPKMHTVNGYVNRSLPGL |
| | IGCHRKSVYWHVIGMGTTPEVHSIFLEGHTFLVRNHRQASLEIS |
| | PITFLTAQTLLMDLGQFLLFCHISSHQHDGMEAYVKVDSCPEEP |
| | QLRMKNNEEAEDYDDDLTDSEMDVVRFDDDNSPSFIQIRSVAKK |
| | HPKTWVHYIAAEEEDWDYAPLVLAPDDRSYKSQYLNNGPQRIGR |
| | KYKKVRFMAYTDETFKTREAIQHESGILGPLLYGEVGDTLLIIF |
| | KNQASRPYNIYPHGITDVRPLYSRRLPKGVKHLKDFPILPGEIF |
| | KYKWTVTVEDGPTKSDPRCLTRYYSSFVNMERDLASGLIGPLLI |
| | CYKESVDQRGNQIMSDKRNVILFSVFDENRSWYLTENIQRFLPN |
| | PAGVQLEDPEFQASNIMHSINGYVFDSLQLSVCLHEVAYWYILS |
| | IGAQTDFLSVFFSGYTFKHKMVYEDTLTLFPFSGETVFMSMENP |
| | GLWILGCHNSDFRNRGMTALLKVSSCDKNTGDYYEDSYEDISAY |
| | LLSKNNAIEPRSFS*GGGS*QVQLVQSGGGLVQAGDSLRLSCAASG |
| | RTFIRYAMAWFRQAPGKEREFVAAIPQSGGRSYYADSVKGRFTI |
| | SRDNAKNTVYLQMNSLKPEDTAVYSCAATSTYYGRSAYSSHSGG |
| | YDYWGQGTQVTVSS*GGGSGGGSGGGSGGGS*QVQLVQSGGGLVQA |
| | GDSLRLSCAASGRTFIRYAMAWFRQAPGKEREFVAAIPQSGGRS |
| | YYADSVKGRFTISRDNAKNTVYLQMNSLKPEDTAVYSCAATSTY |
| | YGRSAYSSHSGGYDYWGQGTQVTVSS*GGGSGGGSGGGSGGGSGG* |
| | *GSGGGS*EITRTTLQSDQEEIDYDDTISVEMKKEDFDIYDEDENQ |
| | SPRSFQKKTRHYFIAAVERLWDYGMSSSPHVLRNRAQSGSVPQF |
| | KKVVFQEFTDGSFTQPLYRGELNEHLGLLGPYIRAEVEDNIMVT |

TABLE K-continued

| Sequences of FVIII_KB0013bv(6GGGS)_Cter-0013bv |
|---|

| FVIII_KB0013bv (6GGGS)_Cter-0013bv | Sequence |
|---|---|
| | FRNQASRPYSFYSSLISYEEDQRQGAEPRKNFVKPNETKTYFWK VQHHMAPTKDEFDCKAWAYFSDVDLEKDVHSGLIGPLLVCHTNT LNPAHGRQVTVQEFALFFTIFDETKSWYFTENMERNCRAPCNIQ MEDPTFKENYRFHAINGYIMDTLPGLVMAQDQRIRWYLLSMGSN ENIHSIHFSGHVFTVRKKEEYKMALYNLYPGVFETVEMLPSKAG IWRVECLIGEHLHAGMSTLFLVYSNKCQTPLGMASGHIRDFQIT ASGQYGQWAPKLARLHYSGSINAWSTKEPFSWIKVDLLAPMIIH GIKTQGARQKFSSLYISQFIIMYSLDGKKWQTYRGNSTGTLMVF FGNVDSSGIKHNIFNPPIIARYIRLHPTHYSIRSTLRMEWMGCD LNSCSMPLGMESKAISDAQITASSYFTNMFATWSPSKARLHLQG RSNAWRPQVNNPKEWLQVDFQKTMKVTGVTTQGVKSLLTSMYVK EFLISSSQDGHQWTLFFQNGKVKVFQGNQDSFTPVVNSLDPPLL TRYLRIHPQSWVHQIALRMEVLGCEAQDLYLTPRGVRL*GGGSGG GSGGGGSGGGS*QVQLVQSGGGLVQAGDSLRLSCAASGRTFIRYAM AWFRQAPGKEREFVAAIPQSGGRSYYADSVKGRFTISRDNAKNT VYLQMNSLKPEDTAVYSCAATSTYYGRSAYSSHSGGYDYWGQGT QVTVSS*GGGSGGGSGGGSGGGS*QVQLVQSGGGLVQAGDSLRLSC AASGRTFIRYAMAWFRQAPGKEREFVAAIPQSGGRSYYADSVKG RFTISRDNAKNTVYLQMNSLKPEDTAVYSCAATSTYYGRSAYSS HSGGYDYWGQGTQVTVSS* |

Italic: GGGS-linker
Bold: sequence KB-VWF-013
Underline: thrombin-cleavage site

In a particular embodiment, two sdAb directed against VWF are inserted within the B-domain of FVIII, while two sdAb are inserted at the C-terminus (FVIII_KB0013bv (6GGGS)_Cter-0013bv_Y1680F) (SEQ ID NO: 23). The linker between sdAb sequence and FVIII light chain contains 6 GGGS-sequences instead of 1. The Y1680F mutation allows to avoid natural binding of FVIII to VWF (binding is only mediated by sdAb). The C-terminal thrombin cleavage site allows to release sdAb upon FVIII activation.

TABLE L

| Sequences of FVIII_KB0013bv(6GGGS)_Cter-0013bv_Y1680F |
|---|

| FVIIL_KB0013bv (6GGGS)_Cter-0013bv_Y1680F | Sequence |
|---|---|
| Polypeptide | SEQ ID NO: 23 MQIELSTCFFLCLLRFCFSATRRYYLGAVELSWDYMQSDLGELP VDARFPPRVPKSFPFNTSVVYKKTLFVEFTDHLFNIAKPRPPWM GLLGPTIQAEVYDTVVITLKNMASHPVSLHAVGVSYWKASEGAE YDDQTSQREKEDDKVFPGGSHTYVWQVLKENGPMASDPLCLTYS YLSHVDLVKDLNSGLIGALLVCREGSLAKEKTQTLHKFILLFAV FDEGKSWHSETKNSLMQDRDAASARAWPKMHTVNGYVNRSLPGL IGCHRKSVYWHVIGMGTTPEVHSIFLEGHTFLVRNHRQASLEIS PITFLTAQTLLMDLGQFLLFCHISSHQHDGMEAYVKVDSCPEEP QLRMKNNEEAEDYDDDLTDSEMDVVRFDDDNSPSFIQIRSVAKK HPKTWVHYIAAEEEDWDYAPLVLAPDDRSYKSQYLNNGPQRIGR KYKKVRFMAYTDETFKTREAIQHESGILGPLLYGEVGDTLLIIF KNQASRPYNIYPHGITDVRPLYSRRLPKGVKHLKDFPILPGEIF KYKWTVTVEDGPTKSDPRCLTRYYSSFVNMERDLASGLIGPLLI CYKESVDQRGNQIMSDKRNVILFSVFDENRSWYLTENIQRFLPN PAGVQLEDPEFQASNIMHSINGYVFDSLQLSVCLHEVAYWYILS IGAQTDFLSVFFSGYTFKHKMVYEDTLTLFPFSGETVFMSMENP GLWILGCHNSDFRNRGMTALLKVSSCDKNTGDYYEDSYEDISAY LLSKNNAIEPRSFS*GGGS*QVQLVQSGGGLVQAGDSLRLSCAASG RTFIRYAMAWFRQAPGKEREFVAAIPQSGGRSYYADSVKGRFTI SRDNAKNTVYLQMNSLKPEDTAVYSCAATSTYYGRSAYSSHSGG YDYWGQGTQVTVSS*GGGSGGGSGGGSGGGS*QVQLVQSGGGLVQA GDSLRLSCAASGRTFIRYAMAWFRQAPGKEREFVAAIPQSGGRS YYADSVKGRFTISRDNAKNTVYLQMNSLKPEDTAVYSCAATSTY YGRSAYSSHSGGYDYWGQGTQVTVSS*GGGSGGGSGGGSGGGSGG GSGGGS*EITRTTLQSDQEEIDYDDTISVEMKKEDFDIFDEDENQ SPRSFQKKTRHYFIAAVERLWDYGMSSSPHVLRNRAQSGSVPQF KKVVFQEFTDGSFTQPLYRGELNEHLGLLGPYIRAEVEDNIMVT |

TABLE L-continued

| Sequences of FVIII_KB0013bv(6GGGS)_Cter-0013bv_Y1680F | |
|---|---|
| FVIIL_KB0013bv (6GGGS)_Cter-0013bv_Y1680F | Sequence |
| | FRNQASRPYSFYSSLISYEEDQRQGAEPRKNFVKPNETKTYFWK VQHHMAPTKDEFDCKAWAYFSDVDLEKDVHSGLIGPLLVCHTNT LNPAHGRQVTVQEFALFFTIFDETKSWYFTENMERNCRAPCNIQ MEDPTFKENYRFHAINGYIMDTLPGLVMAQDQRIRWYLLSMGSN ENIHSIHFSGHVFTVRKKEEYKMALYNLYPGVFETVEMLPSKAG IWRVECLIGEHLHAGMSTLFLVYSNKCQTPLGMASGHIRDFQIT ASGQYGQWAPKLARLHYSGSINAWSTKEPFSWIKVDLLAPMIIH GIKTQGARQKFSSLYISQFIIMYSLDGKKWQTYRGNSTGTLMVF FGNVDSSGIKHNIFNPPIIARYIRLHPTHYSIRSTLRMEWMGCD LNSCSMPLGMESKAISDAQITASSYFTNMFATWSPSKARLHLQG RSNAWRPQVNNPKEWLQVDFQKTMKVTGVTTQGVKSLLTSMYVK EFLISSSQDGHQWTLFFQNGKVKVFQGNQDSFTPVVNSLDPPLL TRYLRIHPQSWVHQIALRMEVLGCEAQDLYLTPRGVRL*GGGSGG* *GSGGGSGGGS*QVQLVQSGGGLVQAGDSLRL*SCAASGRTFIRYAM AWFRQAPGKEREFVAAIPQSGGRSYYADSVKGRFTISRDNAKNT VYLQMNSLKPEDTAVYSCAATSTYYGRSAYSSHSGGYDYWGQGT QVTVSS*GGGSGGGSGGGSGGGS*QVQLVQSGGGLVQAGDSLRLSC AASGRTFIRYAMAWFRQAPGKEREFVAAIPQSGGRSYYADSVKG RFTISRDNAKNTVYLQMNSLKPEDTAVYSCAATSTYYGRSAYSS HSGGYDYWGQGTQVTVSS*** |

Italic: GGGS-linker
Bold: sequence KB-VWF-013
Underline: thrombin-cleavage site
Bold underline: mutation p.Y1680F In a particular embodiment, the clotting factor is FVII. The terms "Factor VII" and "FVII" are used interchangeably herein. Factor VII is a trace plasma glycoprotein that circulates in blood as a single-chain zymogen. The zymogen is catalytically inactive. Single-chain Factor VII may be converted to two-chain Factor VIIa by Factor Xa, Factor XIIa, Factor IXa or thrombin in vitro. Factor Xa is believed to be the major physiological activator of Factor VII. Like several other plasma proteins involved in haemostasis, Factor VII is dependent on vitamin K for its activity, which is required for the γ-carboxylation of multiple glutamic acid residues that are clustered in the amino terminus of the protein. These γ-carboxylated glutamic acids are required for the metal-associated interaction of Factor VII with phospholipids.

The conversion of zymogen Factor VII into the activated two-chain molecule occurs by cleavage of an internal peptide bond located approximately in the middle of the molecule. In human Factor VII, the activation cleavage site is at Arg152-Ile153. In the presence of tissue Factor, phospholipids and calcium ions, the two-chain Factor VIIa rapidly activates Factor X or Factor IX by limited proteolysis. Commercially available therapeutic FVII products include plasma derived FVII (pdFVII), such as Factor VII® (=Immuseven commercialized by Baxter) and recombinant FVII (rFVII) products, such as NovoSeven® which is commercialized by NovoNordisk, and other recombinant FVII products which are on clinical trials: prLA-rFVIIa of Novonordisk (phase I/II trial), CSL689 rVIIa-FP of CSL Behring (phase II/III trial), BAX 817 of Baxter (phase III trial), LR769 of rEVO Biologics and LFB Biotechnologies (phase III trial), BAY 86-6150 eptacog alfa of Bayer (phase II/III trail), Factor VIIa-CTP of OPKO Health (phase II trial) or PF-05280602 of Pfizer (phase I trial).

In certain embodiments, the polypeptide comprises a FVII polypeptide and at least one sdAb directed against VWF according to the invention, wherein said FVII polypeptide comprises Gla domain, hydrophobic region, EGF1 and EGF2 domains, catalytic domains (His-Asp-Ser) and wherein said at least one single-domain antibody directed against VWF is linked to said FVII polypeptide at the C-terminus of said FVII polypeptide.

The typical half-life of a human FVII in humans is several hours (4.2 hours, Osterm et al 2007, Thromb Haemostas vol 98, pp 790-797). In some embodiments, the chimeric FVII polypeptide has extended half-life compared to wild type FVII polypeptide. In certain embodiments, the half-life of the chimeric FVII polypeptide is extended at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than wild type FVII.

In a particular embodiment, the sdAb directed against VWF are inserted at the C-ter domain of factor VII (FVII-KB13-bv) (SEQ ID NO: 14).

TABLE M

| Sequences of FVII-KB13-bv | |
|---|---|
| FVII-KB13-bv | Sequence |
| Polypeptide | SEQ ID NO: 14 MVSQALRLLCLLLGLQGCLAAGGVAKASGGETRDMPWKPGPHRVF VTQEEAHGVLHRRRRANAFLEELRPGSLERECKEEQCSFEEAREI FKDAERTKLFWISYSDGDQCASSPCQNGGSCKDQLQSYICFCLPA |

TABLE M-continued

| Sequences of FVII-KB13-bv | |
|---|---|
| FVII-KB13-bv | Sequence |
| | FEGRNCETHKDDQLICVNENGGCEQYCSDHTGTKRSCRCHEGYSL
LADGVSCTPTVEYPCGKIPILEKRNASKPQGRIVGGKVCPKGECP
QVLLLVNGAQLCGGTLINTIWVVSAAHCFDKIKNWRNLIAVLGEH
DLSEHDGDEQSRRVAQVIIPSTYVPGTTNHDIALLRLHQPVVLTD
HVVPLCLPERTFSERTLAFVRFSLVSGWGQLLDRGATALELMVLN
VPRLMTQDCLQQSRKVGDSPNITEYMFCAGYSDGSKDSCKGDSGG
PHATHYRGTWYLTGIVSWGQGCATVGHFGVYTRVSQYIEWLQKLM
RSEPRPGVLLRAPFPLTPRGVRLGGGSGGGSGGGSGGGSQVQLVQ
SGGGLVQAGDSLRLSCAASGRTFIRYAMAWFRQAPGKEREFVAAI
PQSGGRSYYADSVKGRFTISRDNAKNTVYLQMNSLKPEDTAVYSC
AATSTYYGRSAYSSHSGGYDYWGQGTQVTVSSGGGSGGGSGGGSG
GGSQVQLVQSGGGLVQAGDSLRLSCAASGRTFIRYAMAWFRQAPG
KEREFVAAIPQSGGRSYYADSVKGRFTISRDNAKNTVYLQMNSLK
PEDTAVYSCAATSTYYGRSAYSSHSGGYDYWGQGTQVTVSS |

In a particular embodiment, the chimeric polypeptide according to the invention, wherein two sdAb directed against VWF: i) are replacing the C-terminal part of the B domain of factor VIII (FVIII-KB13-bv) (SEQ ID NO: 13; SEQ ID NO: 16; SEQ ID NO: 17); ii) are fused to the C-terminus of FVIII (SEQ ID NO: 18; SEQ ID NO: 19); iii) are simultaneously replacing the C-terminal part of the B domain of factor VIII and fused to C-terminus of factor VIII (SEQ ID NO: 20; SEQ ID NO: 21; SEQ ID NO 22; SEQ ID NO 23); or iv) are inserted at the C-terminus of factor VII (SEQ ID NO: 14).

In a particular embodiment, the chimeric polypeptide according to the invention, wherein the polypeptide comprises at least one single-domain antibody directed against a first antigen and at least one further binding site directed against a second antigen.

According to the invention, the single domain antibodies and polypeptides of the invention may be produced by conventional automated peptide synthesis methods or by recombinant expression. General principles for designing and making proteins are well known to those of skill in the art.

The single domain antibodies and polypeptides of the invention may be synthesized in solution or on a solid support in accordance with conventional techniques. Various automatic synthesizers are commercially available and can be used in accordance with known protocols as described in Stewart and Young; Tam et al., 1983; Merrifield, 1986 and Barany and Merrifield, Gross and Meienhofer, 1979. The single domain antibodies and polypeptides of the invention may also be synthesized by solid-phase technology employing an exemplary peptide synthesizer such as a Model 433A from Applied Biosystems Inc. The purity of any given protein; generated through automated peptide synthesis or through recombinant methods may be determined using reverse phase HPLC analysis. Chemical authenticity of each peptide may be established by any method well known to those of skill in the art.

As an alternative to automated peptide synthesis, recombinant DNA technology may be employed wherein a nucleotide sequence which encodes a polypeptide of choice is inserted into an expression vector, transformed or transfected into an appropriate host cell and cultivated under conditions suitable for expression as described herein below. Recombinant methods are especially preferred for producing longer polypeptides.

A variety of expression vector/host systems may be utilized to contain and express the peptide or protein coding sequence. These include but are not limited to microorganisms such as bacteria transformed with recombinant bacteriophage, plasmid or cosmid DNA expression vectors; yeast transformed with yeast expression vectors (Giga-Hama et al., 1999); insect cell systems infected with virus expression vectors (e.g., baculovirus, see Ghosh et al., 2002); plant cell systems transfected with virus expression vectors (e.g., cauliflower mosaic virus, CaMV; tobacco mosaic virus, TMV) or transformed with bacterial expression vectors (e.g., Ti or pBR322 plasmid; see e.g., Babe et al., 2000); or animal cell systems. Those of skill in the art are aware of various techniques for optimizing mammalian expression of proteins, see e.g., Kaufman, 2000; Colosimo et al., 2000. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells. Exemplary protocols for the recombinant expression of the peptide substrates or fusion polypeptides in bacteria, yeast and other invertebrates are known to those of skill in the art and a briefly described herein below. Mammalian host systems for the expression of recombinant proteins also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, and the like have specific cellular machinery and characteristic mechanisms for such post-translational activities and may be chosen to ensure the correct modification and processing of the introduced, foreign protein.

In the recombinant production of the single domain antibodies and polypeptides of the invention, it would be necessary to employ vectors comprising polynucleotide molecules for encoding the single domain antibodies and polypeptides of the invention. Methods of preparing such vectors as well as producing host cells transformed with such vectors are well known to those skilled in the art. The polynucleotide molecules used in such an endeavor may be joined to a vector, which generally includes a selectable marker and an origin of replication, for propagation in a host. These elements of the expression constructs are well known to those of skill in the art. Generally, the expression vectors include DNA encoding the given protein being operably linked to suitable transcriptional or translational regulatory sequences, such as those derived from a mammalian, microbial, viral, or insect genes. Examples of regulatory sequences include transcriptional promoters, operators, or enhancers, mRNA ribosomal binding sites, and appropriate sequences which control transcription and translation.

The terms "expression vector," "expression construct" or "expression cassette" are used interchangeably throughout this specification and are meant to include any type of genetic construct containing a nucleic acid coding for a gene product in which part or all of the nucleic acid encoding sequence is capable of being transcribed.

The choice of a suitable expression vector for expression of the peptides or polypeptides of the invention will of course depend upon the specific host cell to be used, and is within the skill of the ordinary artisan.

Expression requires that appropriate signals be provided in the vectors, such as enhancers/promoters from both viral and mammalian sources that may be used to drive expression of the nucleic acids of interest in host cells. Usually, the nucleic acid being expressed is under transcriptional control of a promoter. A "promoter" refers to a DNA sequence recognized by the synthetic machinery of the cell, or introduced synthetic machinery, required to initiate the specific transcription of a gene. Nucleotide sequences are operably linked when the regulatory sequence functionally relates to the DNA encoding the protein of interest (e.g., a single domain antibody). Thus, a promoter nucleotide sequence is operably linked to a given DNA sequence if the promoter nucleotide sequence directs the transcription of the sequence.

Chimeric Polypeptide/VWF Complexes According to the Invention

In another aspect, the invention relates to a chimeric polypeptide/VWF complex wherein the chimeric polypeptide is a chimeric polypeptide of the invention above-described and a VWF polypeptide with extended half-life.

As used herein, the term "VWF polypeptide with extended half-life" refers to variants of VWF or fragments thereof (including especially D'D3 domain) with insertions, deletions and substitutions, either conservative or non-conservative, where such changes do not alter the biological activities of VWF, or derivatives of WVF such as Fc-fusion, leading to an extended half-life compared to the native VWF. The typical half-life of a human VWF in humans is 16 hours (Goudemand et al 2005).

In one embodiment, the VWF polypeptide with extended half-life is a PEGylated rVWF (PEGrVWF).

Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications.

In a particular embodiment, the VWF polypeptide with extended half-life is a PEGylated VWF D'D3.

In a particular embodiment, the VWF polypeptide with extended half-life is a VWF D'D3 conjugated to albumin (D'D3-Alb).

In a particular embodiment, the VWF polypeptide with extended half-life is VWF D'D3-Fc (VWF D'D3-Fc has a prolonged half-life relative to VWF D'D3 because of interactions with the Fc receptor FcRn recycling pathway)[3].

Other possibilities of modifications to prolong the half-life of VWF or VWF D'D3 are HEPylation, polysialylation or the attachment of XTEN-polypeptides.

Therapeutic Methods and Uses

In another aspect, the invention relates to an isolated single-domain antibody (sdAb) directed against von Willebrand Factor (VWF) D'D3 domain for use as drug.

In another aspect, the invention relates to a chimeric polypeptide comprising a polypeptide and at least one single-domain antibody of the invention for use as drug.

In still another aspect, the invention relates to a chimeric polypeptide/VWF complex of the invention for use as drug.

According to the invention, a single domain antibody of the invention or a chimeric polypeptide of the invention, or a chimeric polypeptide/VWF complex of the invention is administered to the patient with a therapeutically effective amount.

In a particular embodiment, the isolated sdAb directed against VWF D'D3 domain according to the invention, a chimeric polypeptide comprising a polypeptide and at least one sdAb directed against VWF according to the invention, or the chimeric polypeptide/VWF complex according to the invention for use in a method for preventing or treating bleeding disorders.

In another embodiment, the invention is suitable for a method of preventing or treating bleeding disorders in a subject in need thereof, comprising administering to said subject a therapeutically effective amount of a chimeric polypeptide according to the invention or a chimeric polypeptide/VWF complex as described above.

For instance the modified clotting factors according to the invention may be used in a method for preventing and/or treating bleeding disorders. The bleeding disorders that may be treated by administration of the modified clotting factors of the invention include, but are not limited to, hemophilia, as well as deficiencies or structural abnormalities in fibrinogen, prothrombin, Factor V, Factor VII or Factor X.

In a particular embodiment, the bleeding disorders that may be treated by administration of the modified clotting factors of the invention is hemophilia A or hemophilia B.

By a "therapeutically effective amount" is meant a sufficient amount of the polypeptide (or the nucleic acid encoding for the polypeptide) to prevent for use in a method for the treatment of acute exacerbation of chronic obstructive pulmonary disease at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular patient will depend upon a variety of factors including the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Another aspect relates to a pharmaceutical composition comprising a single-domain antibody directed against VWF D'D3 domain, a chimeric polypeptide, a chimeric polypeptide/VWF complex as described herein, and a pharmaceutically acceptable carrier.

The single-domain antibodies and polypeptides of the invention (or the nucleic acid encoding thereof) may be combined with pharmaceutically acceptable excipients, and optionally sustained-release matrices, such as biodegradable polymers, to form pharmaceutical compositions. As used herein, the terms "pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The polypeptide (or nucleic acid encoding thereof) can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The polypeptide (or nucleic acid encoding thereof) may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered. The invention will be further illustrated by the following figures and examples.

Methods of Extending or Increasing Half-Life of a Therapeutic Polypeptide

Also disclosed is a method of extending or increasing half-life of a therapeutic polypeptide comprising a step of adding to the polypeptide sequence of said therapeutic polypeptide at least one single-domain antibody directed against VWF D'D3 domain.

In one embodiment, said at least one single-domain antibody directed against VWF is fused or inserted in the polypeptide sequence of said therapeutic polypeptide as above-described. In a particular embodiment, said at least one single-domain antibody directed against VWF is inserted within the B domain of factor VIII as above-described.

Methods for Reducing the Formation of Allo-Antibodies

In some embodiments, the sdAbs of the invention are suitable to reduce the formation of allo-antibodies. In a particular embodiment, at least one single-domain antibody directed against VWF is inserted within the B domain of factor VIII as above-described to reduce the formation of allo-antibodies.

The term "allo-antibodies" has the general meaning in the art and refers to an antibody that occurs naturally against foreign tissues from a person of the same species. Typically, in the context of the invention, incorporating sdAbs against VWF in the FVIII protein avoid the dissociation of FVIII from VWF (FVIII-KB013bv), thus, the subject does not develop allo-antibodies against FVIII-KB013bv which is less immunogenic compared to FVIII that displays normal association-dissociation kinetics.

The invention will be further illustrated by the following figures and examples. However, these examples and figures should not be interpreted in any way as limiting the scope of the present invention.

FIGURES

FIG. 1: Real-time analysis of association and dissociation of VWF interactions with FVIII and sdAbs. Association and dissociation curves for the binding of VWF to immobilized sdAbs and the binding of FVIII to immobilized VWF are plotted in FIG. 1. For the analysis, we focused on the dissociation phase. Apparent dissociation constants were $2.0\pm1.1\times10$-5 s-1 (KB-VWF-008), $0.6\pm0.5\times10$-5 s-1 (KB-VWF-011), $1.3$-$3.5\times10$-5 s-1 (KB-VWF013) and $2.2$-$3.0\times10$-3 s-1 (FVIII).

Figure 2:
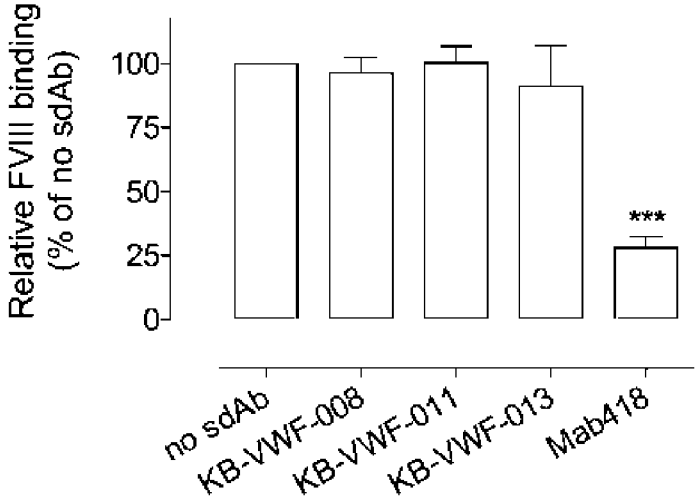

FIG. 2: Effect of sdAbs on VWF binding to Factor VIII. Binding of FVIII to immobilized VWF was determined in the absence or presence of sdAbs or Mab418. Plotted is the percentage FVIII binding relative to FVIII binding in the absence of antibodies. FVIII binding is unaffected by the presence of KB-VWF-008, -011 or -013.

Figure 3:
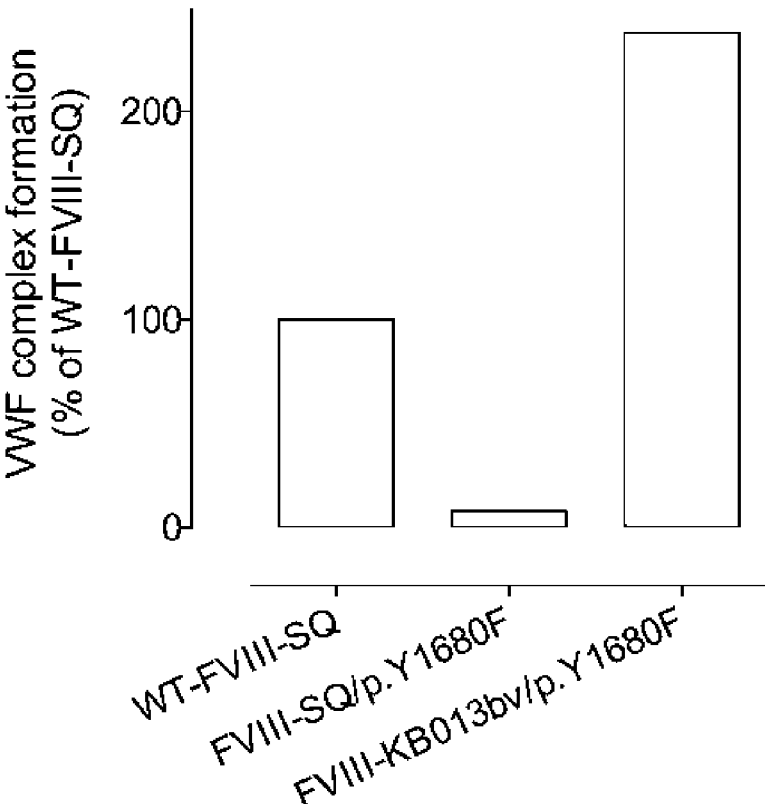

FIG. 3: Factor VIII-sdAb fusion protein binds to VWF. The ability to form a complex with VWF was tested via transient expression of WT-FVIII-SQ, FVIII-SQ/p.Y1680F or FVIII-KB013bv/p.Y1680F in hemophilic mice. Four days after gene transfer, VWF/FVIII complexes were determined, which are expressed as the percentage of complex relative to WT-FVIII-SQ. As expected, the presence of the p.Y1680F mutation abrogated binding of FVIII to VWF (FVIII-SQ/p.Y1680F). In contrast, the introduction of KB-VWF-013 restored and even improved binding to VWF despite the presence of the p.Y1680F mutation.

Figure 4:
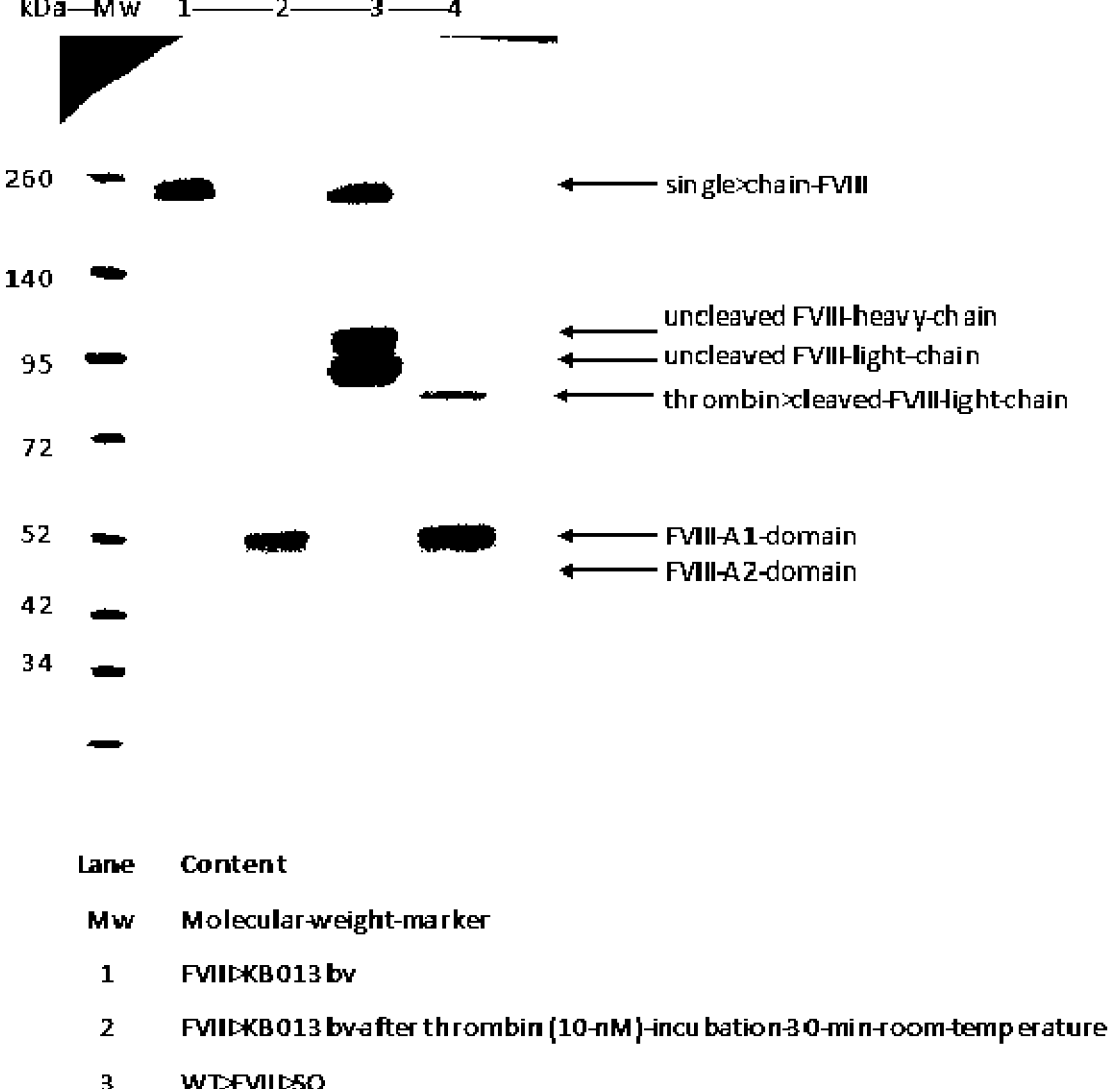

FIG. 4: Expression and functional analysis of FVIII-KB013bv. Purified FVIII-KB013 and WT-FVIII-SQ were incubated in the absence or presence of thrombin. Western blot analysis was performed to determine the presence of FVIII fragments. FVIII-KB013bv migrates predominantly as a single-chain protein when incubated in the absence of thrombin (lane 1), whereas WT-FVIII-SQ predominantly migrates as a heterodimeric protein (lane 3). After thrombin incubation, both FVIII-KB013bv and WT-FVIII-SQ are present as a heterodimeric protein, consisting of the thrombin-cleaved light chain and the heavy-chain derived A1 and A2 domains (lanes 2 & 4).

Figure 5:
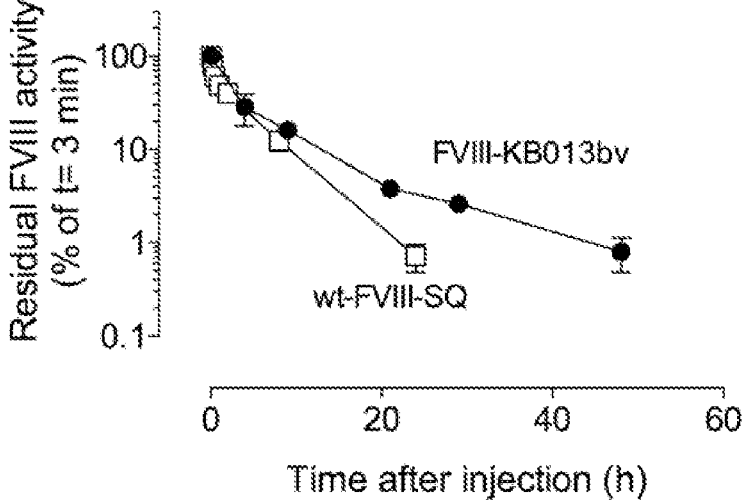

FIG. 5: in vivo survival of FVIII-KB-013bv. FVIII-KB013bv or WT-FVIII-SQ were given intravenously to FVIII-deficient mice. At indicate time-points, blood was collected and FVIII activity was determined. Residual activity relative to activity at 3 min after injection is plotted against time after injection. FVIII-KB013bv is removed from the circulation slower than is WT-FVIII-SQ.

Figure 6:
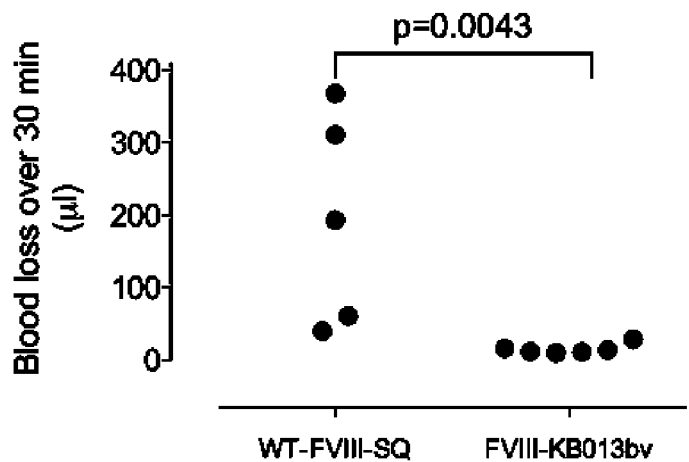

FIG. 6: Correction of hemostasis in hemophilic mice 24 h after injection of FVIII-KB013bv. FVIII-KB013bv or B-domainless FVIII (Xyntha) were given intravenously to FVIII-deficient mice and 24 h after injection the terminal tip of the tail was amputated in anesthetized mice. Blood loss was monitored for 30 min. The volume of shed blood was determined and is presented for each mouse. Mice treated with FVIII-KB013bv lost significantly less blood compared to mice treated with wild-type B-domainless FVIII.

Figure 7:
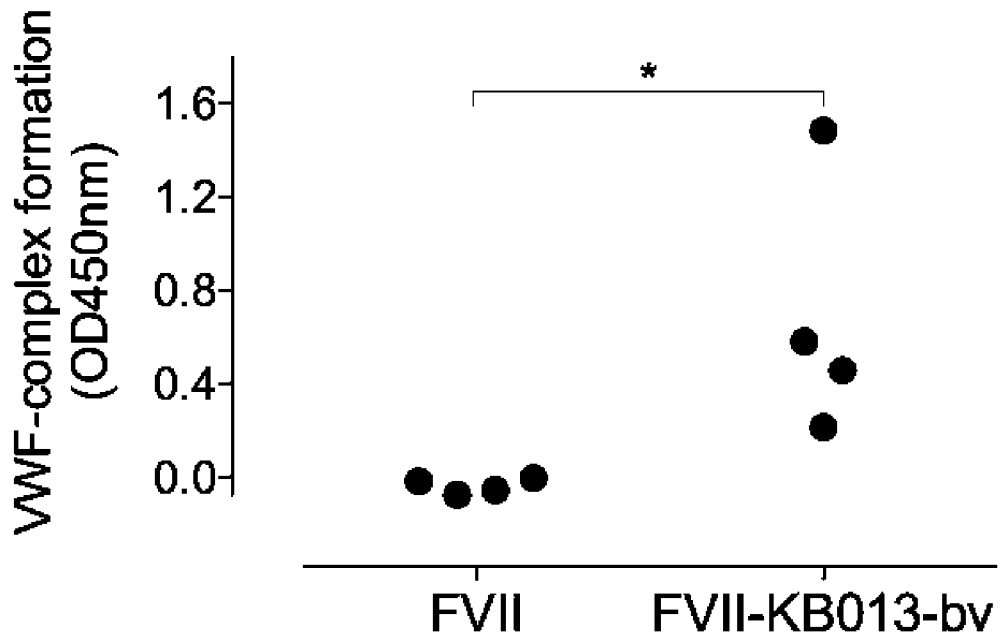

FIG. 7: Fusion of KB-VWF-013 to coagulation factor VII induces complex formation with VWF. The ability to form a complex with VWF was tested via transient expression of wild-type FVII and FVII-KB013-bv in wild-type C57B16 mice. Four days after gene transfer, VWF/FVIII complexes were determined, which are expressed as OD450 nm. As expected, no complex formation with VWF could be detected for wild-type FVII. In contrast, VWF-FVII complexes were detected in all mice expressing FVII-KB013-bv. Thus, the fusion of FVII to KB-VWF-013 induces the capacity of FVII to bind to VWF.

EXAMPLES

Example A: Protein Domain Structure of VWF

Bio-informatic analysis of the cDNA and protein sequences of VWF has revealed that the protein architecture distinguishes different types of domain structures. Originally, this domain structure consisted of a signal peptide (SP), A-domains, B-domains, C-domains, D-domains and a CK-domain arranged in the order: SP-D1-D2-D'-D3-A1-A2-A3-D4-B1-B2-B3-C1-C2-CK (Verweij C L et al. (1986) EMBO Journal, vol. 5, pp. 1839-1847). More recently an updated domain organization has been proposed, in which the domains are arranged in the following order: SP-D1-

D2-D'-D3-A1-A2-A3-D4-C1-C2-C3-C4-C5-C6-CK (Zhou Y F et al. (2012) Blood, vol 120, pp. 449-458). Since the boundaries of the different domains may be varying from one publication to another, we use in this application the boundaries as defined in FIG. 1 of Lenting P J et al. (2015) Blood, vol 125, pp. 2019-2028).

Example B: Binding of sdAb to VWF or Fragments Thereof sdAbs KB-VWF-008, -011 and -013 were immobilized (5 µg/ml) in 10 mM NaHCO3, 50 mM Na2CO3 (pH 9.5) in a volume of 50 µl in half-well microtiter plates (Greiner Bio-One, Les Ulis, France) for 16 h at 4° C. As a positive control, polyclonal rabbit anti-VWF antibodies (Dako, Glostrup, Danmark) were immobilized in a similar fashion. As a negative control, no antibodies were immobilized. After washing the wells three times with 75 µl/well using Tris-buffered saline (pH 7.6) supplemented with 0.1% Tween-20 (TBS-T), wells were blocked with 75 µl/well of TBS-T supplemented with 3% bovine serum albumin (BSA) for 30 min at 37° C. Wells were washed as described above, and subsequently the following VWF preparations (diluted in Tris-buffered saline (pH 7.6) supplemented with 3% BSA, all at 2 µg/ml, 50 µl per well, 2 hours at 37° C.) were added to each of the immobilized sdAbs and both types of control wells:

purified recombinant human VWF (rhVWF),
 purified recombinant murine VWF (rmVWF),
 VWF fragment SpII (a proteolytic fragment of plasma-derived (pd)-VWF following incubation with *S. aureus* V8-protease, which encompasses residues 2129-2813 of VWF; Denis C et al. (1993) Arteriosclerosis Thrombosis, vol 13, pp. 398-406), hD1-D2-HPC4 fragment (human VWF residues 23-762 fused to the amino acid sequence EDQVDPRLIDGK), mD1-D2-HPC4 fragment (murine VWF residues 23-762 fused to the amino acid sequence EDQVDPRLIDGK)

Wells were then washed three times with 75 µl/well using TBS-T. Bound VWF preparations were probed with peroxidase-labeled polyclonal rabbit anti-VWF antibodies (Dako, Glostrup, Danmark; diluted 1/6000) for rhVWF, rmVWF, SpII and SPIII or with peroxidase-labeled monoclonal antibody HPC4 (diluted 1/1000) for D'D3-HPC4, A1A2A3-HPC4, hD1D2-HPC4 and mD1-D2-HPC4 for 2 hours at 37° C. with 50 µl per well. Wells were then washed three times with 75 µl/well using TBS-T. Residual peroxidase activity was detected by measuring peroxidase-mediated hydrolysis of 3,3',5,5'-tetramethylbenzidine.

Negative binding (−) was defined as optical density (OD) being ≤0.5, moderate positive binding (+) was defined as OD being >0.5 and <1.0, strongly positive binding (++) was defined as OD being ≥1.0. Based on these definitions, none of the VWF preparations displayed moderate or strongly positive binding to the negative control (Table 1). All VWF preparations with the exception of mD1-D2-HPC4 had moderate or strongly positive binding to the positive control (polyclonal anti-VWF antibodies). None of the sdAbs bound to SpII, A1A2A3-HPC4, hD1-D2-HPC4 or mD1-D2-HPC4. In contrast, KB-VWF-008, -011 and -013 had moderate or strongly positive binding to rhVWF, spIII and D'D3-HPC4, suggesting that the epitope of these three sdAbs is located within VWF residues 764-1247. Furthermore, sdAb KB-VWF-013 was the only one of the three tested sdAbs that reacted positively with rmVWF, showing that this sdAb cross-reacts with murine VWF.

TABLE 1 belonging to example B: Binding of sdAB to VWF and fragments thereof

| sdAb | rhVWF | rmVWF | SpII | SpIII | D'D3-HPC4 | A1A2A3-HPC4 | hD1D2-HPC4 | mD1D2-HPC4 |
|------|-------|-------|------|-------|-----------|-------------|------------|------------|
| 008 | + | − | − | + | ++ | − | − | − |
| 011 | ++ | − | − | + | ++ | − | − | − |
| 013 | ++ | + | − | ++ | ++ | − | − | − |
| Control | ++ | + | ++ | ++ | ++ | ++ | + | − | rhVWF: recombinant humanVWF;
rmVWF: recombinant murine VWF;
spII: a proteolytic fragment of plasma-derived (pd)-VWF following incubation with *S. aureus* V8-protease, which encompasses residues 2129-2813 of VWF;
spIII: a proteolytic fragment of pd-VWF following incubation with *S. aureus* V8-protease, which encompasses residues 764-2128 of VWF;
D'D3-HPC4: human VWF residues 764-1247 fused to the amino acid sequence EDQVDPRLIDGK;
A1-A2-A3-HPC4: human VWF residues 1260-1874 fused to the amino acid sequence EDQVDPRLIDGK;
hD1-D2-HPC4: human VWF residues 23-762 fused to the amino acid sequence EDQVDPRLIDGK;
mD1-D2-HPC4: murine VWF residues 23-762 fused to the amino acid sequence EDQVDPRLIDGK;
control; polyclonal rabbit-antihuman VWF antibodies (Dako).
−: Negative binding defined as OD being ≤0.5;
+: Moderate positive binding defined as OD being >0.5-<1.0;
++: Strongly positive binding defined as being ≥1.0

VWF fragment SpIII (a proteolytic fragment of pd-VWF following incubation with *S. aureus* V8-protease, which encompasses residues 764-2128 of VWF; Kalafatis M et al. (1987) Blood, vol 70, pp. 1577-1583),
 D'D3-HPC4 fragment (human VWF residues 764-1247 fused to the amino acid sequence EDQVDPRLIDGK (SEQ ID NO: 15), representing a recognition site for antibody HPC4),
 A1-A2-A3-HPC4 fragment (human VWF residues 1260-1874 fused to the amino acid sequence EDQVDPR-LIDGK),

Example C: Real-Time Analysis of Association and Dissociation of VWF Interactions with FVIII and sdAbs The interaction between VWF and sdAbs was analyzed via bio-layer interferometry using Octet-QK equipment (Fortebio, Meldo Park, CA, USA). To this end, sdAbs KB-VWF-008, -011 and -013 were diluted in 0.1 M Mes (pH 5.0) to a concentration of 10 µg/ml for coupling to EDC/NHS-activated amine-reactive biosensors (Fortebio, Menlo Park, CA, USA). Sensors were rehydrated in 0.2 ml 0.1 M MES, pH 5.0 for 300 sec. Sensors were then activated via incubation with 0.1 ml 0.2 M EDC/0.095 M NHS mixture for 300 sec and subsequently incubated with 0.1 ml sdAb-solution for 600 sec. Unoccupied amine-reactive sites were quenched by incubating with 1M ethanolamine for 180 sec, and sensors were allowed to reach stable baseline levels via incubation with phosphate-buffered saline supplemented with 0.1% Tween-20 (PBS-T) for 300 sec. sdAb-coated sensors were then transferred to wells containing various concentrations of purified plasma-derived VWF (2.5, 25 & 250 µg/ml in PBS-T for KB-VWF-008 and -011 versus 25 & 250 µg/ml for KB-VWF-013) and incubated for 600 sec in order to visualize association of VWF to immobilized sdAbs. Following this association phase, sensors were transferred to wells containing PBS-T and incubated for 900 sec, allowing dissociation of the VWF-sdAb complex.

In another set of experiments, we determined the association and dissociation of factor VIII to immobilized recombinant human VWF via biolayer-interferometry analysis, also using Octet-QK equipment Amine-reactive biosensors were used to immobilize recombinant VWF (50 µg/ml in 0.1 M MES, pH 5.0). After hydration of the sensors via a 600-sec incubation with 0.1 M MES pH 5.0, sensors were activated with 0.1 ml 0.2 M EDC/0.095 M NHS mixture for 420 sec and subsequently incubated with 0.1 ml VWF-solution for 420 sec. Unoccupied amine-reactive sites were quenched by incubating with 1M ethanolamine for 420 sec, and sensors were allowed to reach stable baseline levels via incubation with Hepes-buffer (20 mM Hepes, 0.11 M NaCl, 0.005% Tween-20, 5 mM CaCl2, pH 7.3) for 600 sec. VWF-coated sensors were then transferred to wells containing various concentrations of purified recombinant full-length factor VIII (Kogenate; diluted to 3.5 nM or 1.4 nM in Hepes-buffer) and incubated for 600 sec in order to visualize association of FVIII to immobilized VWF. Following this association phase, sensors were transferred to wells containing Hepes-buffer and incubated for 600 sec, allowing dissociation of the VWF-FVIII complex.

Association and dissociation curves are plotted in FIG. 1. When analyzing the data for the interaction between sdAbs and VWF versus the interaction between VWF and FVIII, we focused on the dissociation phase for both types of interaction. The dissociation rate constant for the VWF-FVIII interaction was calculated using an equation for a single exponential decay, and the dissociation rate constants were calculated to be $2.2 \times 10\text{-}3$ s-1 and $3.0 \times 10\text{-}3$ s-1 for FVIII concentrations of 3.5 nM and 1.4 nM, respectively. These values are similar to those described in the literature $(0.3\text{-}6.0 \times 10\text{-}3$ s-1; Sandberg et al (2012) Thromb Res vol 130, pp 808-817; Dimitrov et al (2012) Biochemistry vol 51, pp 4108-4116; Zollner et al (2014) Thromb Res vol 134, pp 125-131). The dissociation constants for the sdAbs were could not be calculated accurately using an equation for a single exponential decay, as the dissociation was too slow during the period that was monitored. We used therefore a linear regression approach to determine the slope of the dissociation curve, which represents an apparent dissociation rate constant that probably over-estimates the true dissociation rate constant (i.e. in reality dissociation is slower than represented by the apparent dissociation rate constant). For KB-VWF-008, the apparent dissociation rate constant was $2.0 \pm 1.1 \times 10\text{-}5$ s-1 (mean±standard deviation; n=3 concentrations). For KB-VWF-011, the apparent dissociation rate constant was $0.6 \pm 0.5 \times 10\text{-}5$ s-1 (mean±standard deviation; n=3 concentrations). For KB-VWF-013, the apparent dissociation rate constants was $1.3 \times 10\text{-}5$ s-1 and $3.5 \times 10\text{-}5$ s-1 (for 250 □g/ml and 25 □g/ml, respectively).

Thus, for each of the three sdAbs, the apparent dissociation rates constants for the interaction with VWF are at least 15-300-fold slower compared to those dissociation rates constants reported in the literature for the FVIII-VWF interaction, and at least 100-fold slower compared to the dissociation rate constant calculated for the VWF-FVIII interaction analyzed in the same Octet-QK equipment.

Example D: Effect of sdAbs on VWF Binding to Factor VIII

Polyclonal rabbit anti-VWF antibodies (Dako, Glostrup, Danmark) were immobilized onto microtiter wells at 5 µg/ml in 50 mM Na2CO3 (pH 9.5) overnight at 4° C. in a volume of 50 µl. After washing thrice with Tris-buffered saline supplemented with 0.1% Tween-20 (TBS-T), wells were saturated with 3% BSA in TBS-T. Then rVWF (0.03-1.0 µg/ml; 50 µl/well) was added to the wells and incubated overnight at 4° C. After washing in TBS-T, wells were incubated twice with 75 µl of 0.35 M CaCl2 for 10 min at 37° C., followed by 6 washes with TBTS-T (75 µl/well). Then rFVIII (Kogenate-FS, Bayer Healthcare) diluted to a concentration of 1.5 U/ml was added in the presence or absence of 20 µg/ml of sdAb KB-VWF-008, -11 or -013 in a total volume of 50 µl. As a control, FVIII was added in the presence of the murine monoclonal anti-VWF antibody Mab418, which blocks binding of FVIII to VWF (Takahashi Y et al. (1987) Blood vol 70, pp 1679-1682). After 2 h at 37° C. and 3 washes with TBS-T (75 µl/well), bound FVIII was probed using peroxidase-labeled polyclonal sheep-anti-FVIII antibodies (Stago BNL, Leiden, the Netherlands) and detected by measuring peroxidase-mediated hydrolysis of 3,3',5,5'-tetramethylbenzidine. For each VWF concentration, FVIII binding in the presence of sdAb or Mab418 was calculated relative to FVIII binding in the absence of sdAb or Mab418, and expressed in percentage binding (FIG. 2). Whereas the presence of Mab418 reduced binding of FVIII to VWF by 72±5% (mean±standard deviation; n=6; p<0.001 compared to control), the presence of each of the sdAbs left FVIII binding similar to that in the absence of any antibody (p>0.05 when tested using one-way ANOVA with multiple comparisons). This shows that sdAbs KB-VWF-008, -011 and -013 do not interfere with the binding of FVIII to VWF.

Example E: Factor VIII-sdAb Fusion Protein Binds to VWF cDNA constructs encoding wild-type B-domainless FVIII (WT-FVIII-SQ), B-domainless FVIII containing a Tyr to Phe replacement at position 1680 (FVIII-SQ/p.Y1680F) and FVIII-KB013bv containing a Tyr to Phe replacement at position 1680 (FVIII-KB013bv/p.Y1680F) were cloned into the pLIVE-plasmid (Mirus Bio, Madison, WI, USA). Tyrosine at position 1680 is sulfated in WT-FVIII-SQ, a requirement for the binding to von Willebrand factor (VWF) and mutation of p.Tyr1680 to Phe is associated with a loss of VWF binding (Leyte A et al. (1991) J Biol Chem vol 266, pp 740-746). Plasmids (100 µg/mouse) were injected into factor VIII-deficient mice via hydrodynamic gene transfer: plasmids are diluted in 0.9% saline with the volume corresponding to 10% of the animal's bodyweight (i.e. 2 ml for a 20-gram mouse). The solution is injected in the tail vein within 5 seconds. Four days after gene transfer, blood was collected via retro-orbital puncture from isoflurane-anesthetized mice and plasma was prepared by centrifugation (1500 g for 20 min at 22° C.). Plasma was then used to measure VWF-FVIII complexes that were formed in the plasma of the mice. Complexes were determined as follows: microtiter wells were coated with polyclonal rabbit anti-VWF antibodies (5 μg/ml) as described in example D. After washing thrice with Tris-buffered saline supplemented with 0.1% Tween-20 (TBS-T), wells were saturated with 3% BSA in TBS-T. Then murine plasma samples (diluted 10-fold in TBS-T) were added to the wells and incubated 2 hours at 37° C. After 3 washes with TBS-T (75 μl/well), bound FVIII was probed using peroxidase-labeled polyclonal sheep-anti-FVIII antibodies (Stago BNL, Leiden, the Netherlands) and detected by measuring peroxidase-mediated hydrolysis of 3,3',5,5'-tetramethylbenzidine. The amount of VWF-complex for mutants FVIII-SQ/p.Y1680F and FVIII-KB013bv/p. Y1680F was related to that of WT-FVIII-SQ, which was arbitrarily set as 100%. As anticipated, complex formation with VWF was strongly reduced for mutant FVIII-SQ/p.Y1680F (8% compared to 100% for WT-FVIII-SQ; see FIG. 3). In contrast, binding was increased 2.4 fold (238%) for variant FVIII-KB013bv/p. Y1680F, which contains the VWF-binding sdAbs. Since the p. Y1680F mutation abrogates natural VWF binding, these data show that while incorporated in the factor VIII protein, sdAb KB-VWF-013 is able to rescue binding to VWF. Thus, in the context of the fusion protein, sdAb KB-VWF-013 contributes to VWF binding.

Example F: Expression and Functional Analysis of FVIII-KB013bv

Baby Hamster Kidney (BHK)-cells were transfected with cDNA encoding FVIII-KB013bv cloned in pcDNA3.1/Hygro and stable cell lines were obtained via selection with hygromycin. One clone was selected for the production of FVIII-KB013bv. FVIII-KB013bv was purified from the culture medium via affinity chromatography using VIIISelect-matrix as instructed by the manufacturer (GE Healthcare, Vélizy-Villacoublay, France). Purified FVIII-KB013bv was tested for activity and antigen. Five top-fractions were selected and chromogenic two-stage activity (Biophen FVIII:C; Hyphen Biomed, Neuville-sur-Oise, France) and factor VIII antigen levels (Girma J P et al (1998) Haemophilia vol 4 pp 98-103) were determined. Average activity was found to be 188±42 U/ml (mean±SD; n=5 consecutive elution fractions) and antigen was calculated to be 176±28 U/ml. Average activity/antigen ratio was 1.1±0.3, showing that FVIII-KB013bv displays full activity in the chromogenic two-stage activity assay.

In a second analysis, FVIII-KB013bv and WT-FVIII-SQ were incubated with in the absence or presence of thrombin (10 nM) for 30 min at room temperature. Subsequently samples were analyzed via Western blotting using polyclonal sheep anti-FVIII antibodies. For samples incubated in the absence of thrombin, WT-FVIII-SQ is predominantly present in a cleaved form, consisting of a 90-kDa heavy chain and an 80-kDa light chain while some uncleaved material was also present (Lane 3 in FIG. 4). In contrast, for FVIII-KB013bv>90% of the preparation was present as a single-chain protein, appearing as a doublet (Lane 1 in FIG. 4). Of note, the size of the uncleaved FVIII-013bv is slightly larger than that of WT-FVIII-SQ, due to the insertion of two copies of sdAb KB-VWF-013 between the FVIII heavy and light chain (Lanes 1 & 3 in FIG. 4). In contrast, following incubation with thrombin, WT-FVIII-SQ and FVIII-013bv displayed a similar pattern for thrombin-activated FVIII, with a 70-kDa light chain and the separate A1 and A2 domains (Lanes 2 & 4 in FIG. 4). This analysis indicates that following thrombin activation, the inserted sdAb KB-VWF- 013bv is removed from the protein, giving rise to the natural heterotrimeric FVIIIa protein.

Example G: In Vivo Survival of FVIII-KB-013bv

Purified WT-FVIII-SQ or FVIII-kb013bv (both produced in BHK-M cells and purified using VIIISelect-affinity chromatography) were given intravenously (250-500 U/kg) to FVIII-deficient mice. At different time-points after injection (3 min, 30 min, 1 h, 2 h, 8 h and 24 h for WT-FVIII-SQ and 3 min, 4 h, 9 h, 21 h, 29 h and 48 h for FVIII-KB013bv) blood samples were obtained via retro-orbital puncture from isoflurane-anesthetized mice and plasma was prepared by centrifugation (1500 g for 20 min at 22° C.). Residual FVIII activity was measured using a chromogenic two-stage assay as instructed by the manufacturer (Biophen FVIII:C; Hyphen Biomed, Neuville-sur-Oise, France). Residual FVIII activity relative to activity at 3 min after injection was plotted against the time after injection (FIG. 5). This approach revealed that activity for FVIII-KB013bv remained higher WT-FVIII-SQ at later time-points. For instance, relative residual FVIII activity for WT-FVIII at 24 h was 0.72±0.23% (n=3), whereas for FVIII-KB013bv the relative residual activity at 29 h was more than 3-fold higher (2.62±0.25%; n=3; p=0.0007 in student t-test). When data where analyzed using an equation describing a single exponential decay (Graph Prism 5 for Mac OSX, GraphPad Software, La Jolla, CA, USA), the half-life calculated for WT-FVIII-SQ was 1.1 h (95% confidence interval 0.9-1.5 h). For FVIII-KB013bv the half-life was calculated to be 2.1 h (95% confidence interval 1.7-2.9 h; p=0.0032 compared to WT-FVIII-SQ), 2-fold longer than the half-life for WT-FVIII-SQ. These results show that the presence of two copies of sdAb KB-VWF-013 has a significant beneficial effect on the survival of FVIII.

Example H: Correction of Haemostasis in Hemophilic Mice 24 h After Injection of FVIII-KB013bv 8-12 week old hemophilic mice were given WT-FVIII-SQ (Xyntha) or FVIII-KB013bv at a dose of 500 U/kg via intravenous tail injection. Twenty-four hours after injection, the terminal 3 mm of the tail-tip was amputated from ketamine/xylazine-anesthetized mice. The amputated tail was immersed immediately after transection in a 50 ml tube full of warm physiological saline. Blood was collected for 30 min at 37° C. After 30 min, the mixture of blood and physiological saline was centrifuged at 1500 g. The red blood cells pellet was then lysed in H2O and the amount of hemoglobin was obtained by reading the absorbance at 416 nm. The volume of blood lost in each sample was calculated from a standard curve, which is obtained by lysing defined volumes (20 μl, 40 μl, 60 μl, 80 μl and 100 μl) of mouse blood in H2O to extract hemoglobin as described above. Blood loss for each mouse is presented in FIG. 6. For mice injected with FVIII-KB013bv, average blood loss was calculated to be 13±3 μl (mean±standard deviation; n=3 mice). For mice that received WT-FVIII-SQ, average blood loss was 194±146 μl (mean±standard deviation; n=5 mice), which is significantly more compared the mice injected with FVIII-KB013bv (p=0.0043 as determined using the Mann-Whitney test). Thus, FVIII-KB013bv displays hemostatic activity for a longer period of time than does WT-FVIII-SQ.

Example I: Use of FVIII-KB013bv as a Therapeutic Protein to Reduce the Formation of Allo-Antibodies Although VWF and FVIII circulate in plasma as a complex, there is a striking difference in the extent by which allo-antibodies develop following therapeutic application of these proteins. Development of allo-antibodies to VWF in response to replacement therapy is estimated to involve 5-10% of the patients with severe von Willebrand disease (James et al (2013) *Blood vol* 122, pp 636-640). In contrast, inhibitory allo-antibodies arise in up to 27% of previously untreated haemophilia A patients (Iorio et al. (2010) *JTH* vol 8, pp 1256-1265).

The underlying reason for this difference in antibody development rate is unknown. Recently, it has been shown by Sorvillo and colleagues (Haematologica 2016 in press; doi:10.3324/haematol.2015.137067) that VWF remains associated at the surface of antigen-presenting cells without being endocytosed. In contrast, FVIII that was bound to this VWF is actually taken up by these cells and processed for incorporation into MHC-class II molecules, thereby allowing presentation to CD4+ T-cells. The notion that FVIII but not VWF enters into antigen-presenting cells could explain the antibody development is increased upon FVIII replacement therapy compared to VWF replacement therapy. A method that prevents dissociation of FVIII at the surface of the antigen presenting cell, and thereby uptake of FVIII by the antigen presenting cell would thus be a means to reduce the formation of allo-antibodies upon FVIII replacement therapy. One way to reduce dissociation of FVIII from VWF is by incorporating sdAbs against VWF in the FVIII protein, and an example hereof is FVIII-KB013bv of the present invention. FVIII-KB013bv could therefore be used as a therapeutic protein that is less immunogenic compared to FVIII that displays normal association-dissociation kinetics.

Example J: Fusion of KB-VWF-013 to Coagulation Factor VII Induces Complex Formation with VWF To determine whether sdAbs recognizing VWF can mediate binding of other proteins than FVIII to VWF, a cDNA was constructed encoding the sequence of human coagulation factor VII (FVII) fused to two copies of KB-VWF-013. Sequences encoding FVII and KB-VWF-013 were separated by a linker-sequence encoding a thrombin-cleavage site. The full sequence of this cDNA and corresponding protein is referred to as FVII-KB13-bv. FVII-KB-13-bv and WT-FVII were cloned into the pLIVE-plasmid (Mirus Bio, Madison, Wis., USA). Plasmids (100 µg/mouse) were injected into wild-type C57B16-mice via hydrodynamic gene transfer: plasmids are diluted in 0.9% saline with the volume corresponding to 10% of the animal's bodyweight (i.e. 2 ml for a 20-gram mouse). The solution is injected in the tail vein within 5 seconds. Four days after gene transfer, blood was collected via retro-orbital puncture from isoflurane-anesthetized mice and plasma was prepared by centrifugation (1500 g for 20 min at 22° C.). Plasma was then used to measure complexes between VWF and FVII or FVII-KB13-by that were formed in the plasma of the mice. Complexes were determined as follows: microtiter wells were coated with polyclonal sheep anti-human FVII antibodies (Affinity Biologicals, Ancaster ON, Canada) at a concentration of 2.5 µg/ml in 50 µl carbonate-buffer (0.07 M NaHCO3, 0.03 M Na2HCO3, pH 9.6) overnight at 4° C. Wells were washed thrice with Tris-buffered saline supplemented with 0.1% Tween-20 (TBS-T), then saturated with 5% BSA, 1% polyvinylpyrrolidone (PVP) in TBS-T for 2 hours at 37° C. and again washed 5 times with TBS-T. Then murine plasma samples (diluted 10-fold in 50 µl TBS-T containing 1% BSA) were added to the wells and incubated 2 hours at 37° C. After 5 washes with TBS-T (75 µl/well), bound FVII or FVII-KB13-bv was probed using peroxidase-labeled polyclonal rabbit anti-VWF antibodies (Dako) and detected by measuring peroxidase-mediated hydrolysis of 3,3',5,5'-tetramethylbenzidine. Whereas for mice expressing FVII no signal above the background could be detected (OD450 nm=−0.038±0.033; mean±standard deviation; n=4 mice), suggesting the absence of complexes between VWF and FVII. In contrast, a clear signal was observed for plasma from each mouse expressing FVII-KB13-bv (OD450 nm=0.684±0.554; n=4; p=0.029 analyzed using Mann-Whitney test). This demonstrates that the fusion of FVII to sdAb KB-VWF-013 induces the protein to associate to circulating VWF.

REFERENCES

Throughout this application, various references describe the state of the art to which this invention pertains. The disclosures of these references are hereby incorporated by reference into the present disclosure.

1. Mei B, Pan C, Jiang H, et al. Rational design of a fully active, long-acting PEGylated factor VIII for hemophilia A treatment. Blood 2010; 116(2):270-279.
2. Dumont J A, Liu T, Low S C, et al. Prolonged activity of a recombinant factor VIII-Fc fusion protein in hemophilia A mice and dogs. Blood 2012; 119(13):3024-3030.
3. Yee A, Gildersleeve R D, Gu S, et al. A von Willebrand factor fragment containing the D'D3 domains is sufficient to stabilize coagulation factor VIII in mice. Blood 2014; 124(3):445-452.

---

SEQUENCE LISTING

```
Sequence total quantity: 23
SEQ ID NO: 1            moltype = AA  length = 9
FEATURE                 Location/Qualifiers
REGION                  1..9
                        note = Synthetic KB-VWF-013 CDR1SEQ ID NO: 1
source                  1..9
                        mol_type = protein
                        organism = synthetic construct
SEQUENCE: 1
GRTFIRYAM                                                              9

SEQ ID NO: 2            moltype = AA  length = 16
FEATURE                 Location/Qualifiers
REGION                  1..16
                        note = Synthetic KB-VWF-013 CDR2 SEQ ID NO: 2
source                  1..16
                        mol_type = protein
```

-continued

```
                              organism = synthetic construct
SEQUENCE: 2
IPQSGGRSYY ADSVKG                                                  16

SEQ ID NO: 3                  moltype = AA  length = 19
FEATURE                       Location/Qualifiers
REGION                        1..19
                              note = Synthetic KB-VWF-013 CDR3 SEQ ID NO: 3
source                        1..19
                              mol_type = protein
                              organism = synthetic construct
SEQUENCE: 3
TSTYYGRSAY SSHSGGYDY                                               19

SEQ ID NO: 4                  moltype = AA  length = 128
FEATURE                       Location/Qualifiers
REGION                        1..128
                              note = Synthetic KB-VWF-013 SEQ ID NO: 4
source                        1..128
                              mol_type = protein
                              organism = synthetic construct
SEQUENCE: 4
QVQLVQSGGG LVQAGDSLRL SCAASGRTFI RYAMAWFRQA PGKEREFVAA IPQSGGRSYY  60
ADSVKGRFTI SRDNAKNTVY LQMNSLKPED TAVYSCAATS TYYGRSAYSS HSGGYDYWGQ 120
GTQVTVSS                                                          128

SEQ ID NO: 5                  moltype = AA  length = 10
FEATURE                       Location/Qualifiers
REGION                        1..10
                              note = Synthetic KB-VWF-008 CDR1 SEQ ID NO:5
source                        1..10
                              mol_type = protein
                              organism = synthetic construct
SEQUENCE: 5
GRTFSDYAMG                                                         10

SEQ ID NO: 6                  moltype = AA  length = 16
FEATURE                       Location/Qualifiers
REGION                        1..16
                              note = Synthetic KB-VWF-008 CDR2 SEQ ID NO: 6
source                        1..16
                              mol_type = protein
                              organism = synthetic construct
SEQUENCE: 6
INRSGGRLSY AESVND                                                  16

SEQ ID NO: 7                  moltype = AA  length = 16
FEATURE                       Location/Qualifiers
REGION                        1..16
                              note = Synthetic KB-VWF-008 CDR3 SEQ ID NO: 7
source                        1..16
                              mol_type = protein
                              organism = synthetic construct
SEQUENCE: 7
RTNWNPPRPL PEEYNY                                                  16

SEQ ID NO: 8                  moltype = AA  length = 125
FEATURE                       Location/Qualifiers
REGION                        1..125
                              note = Synthetic KB-VWF-008 SEQ ID NO: 8
source                        1..125
                              mol_type = protein
                              organism = synthetic construct
SEQUENCE: 8
QVQLVQSGGG LVQAGDSLKL SCAASGRTFS DYAMGCILQN PGKERDFVAS INRSGGRLSY  60
AESVNDLFTI SVDNAKNMLY LQMNSLKPED TAVHYCVLRT NWNPPRPLPE EYNYWGQETQ 120
VTVSS                                                             125

SEQ ID NO: 9                  moltype = AA  length = 10
FEATURE                       Location/Qualifiers
REGION                        1..10
                              note = Synthetic KB-VWF-011 CDR1 SEQ ID NO:9
source                        1..10
                              mol_type = protein
                              organism = synthetic construct
SEQUENCE: 9
GGTFSNYAMG                                                         10

SEQ ID NO: 10                 moltype = AA  length = 16
```

-continued

```
FEATURE           Location/Qualifiers
REGION            1..16
                  note = Synthetic KB-VWF-011 CDR2 SEQ ID NO: 10
source            1..16
                  mol_type = protein
                  organism = synthetic construct
SEQUENCE: 10
ISRSGHRTDY ADSAKG                                                    16

SEQ ID NO: 11     moltype = AA  length = 15
FEATURE           Location/Qualifiers
REGION            1..15
                  note = Synthetic KB-VWF-011 CDR3 SEQ ID NO: 11
source            1..15
                  mol_type = protein
                  organism = synthetic construct
SEQUENCE: 11
RSDWSIATTA TSYDY                                                     15

SEQ ID NO: 12     moltype = AA  length = 124
FEATURE           Location/Qualifiers
REGION            1..124
                  note = Synthetic KB-VWF-011SEQ ID NO: 12
source            1..124
                  mol_type = protein
                  organism = synthetic construct
SEQUENCE: 12
QVQLVQSGGG LVQAGDSLRL SCAASGGTFS NYAMGWFRQT PGKEREFVAR ISRSGHRTDY    60
ADSAKGRFTI SRDNAKNTVY LQMNSLKPED TAVYYCAARS DWSIATTATS YDYWGQGTQV   120
TVSS                                                               124

SEQ ID NO: 13     moltype = AA  length = 1726
FEATURE           Location/Qualifiers
REGION            1..1726
                  note = Synthetic SEQ ID NO: 13
source            1..1726
                  mol_type = protein
                  organism = synthetic construct
SEQUENCE: 13
MQIELSTCFF LCLLRFCFSA TRRYYLGAVE LSWDYMQSDL GELPVDARFP PRVPKSFPFN    60
TSVVYKKTLF VEFTDHLFNI AKPRPPWMGL LGPTIQAEVY DTVVITLKNM ASHPVSLHAV   120
GVSYWKASEG AEYDDQTSQR EKEDDKVFPG GSHTYVWQVL KENGPMASDP LCLTYSYLSH   180
VDLVKDLNSG LIGALLVCRE GSLAKEKTQT LHKFILLFAV FDEGKSWHSE TKNSLMQDRD   240
AASARAWPKM HTVNGYVNRS LPGLIGCHRK SVYWHVIGMG TTPEVHSIFL EGHTFLVRNH   300
RQASLEISPI TFLTAQTLLM DLGQFLLFCH ISSHQHDGME AYVKVDSCPE EPQLRMKNNE   360
EAEDYDDDLT DSEMDVVRFD DDNSPSFIQI RSVAKKHPKT WVHYIAAEEE DWDYAPLVLA   420
PDDRSYKSQY LNNGPQRIGR KYKKVRFMAY TDETFKTREA IQHESGILGP LLYGEVGDTL   480
LIIFKNQASR PYNIYPHGIT DVRPLYSRRL PKGVKHLKDF PILPGEIFKY KWTVTVEDGP   540
TKSDPRCLTR YYSSFVNMER DLASGLIGPL LICYKESVDQ RGNQIMSDKR NVILFSVFDE   600
NRSWYLTENI QRFLPNPAGV QLEDPEFQAS NIMHSINGYV FDSLQLSVCL HEVAYWYILS   660
IGAQTDFLSV FFSGYTFKHK MVYEDTLTLF PFSGETVFMS MENPGLWILG CHNSDFRNRG   720
MTALLKVSSC DKNTGDYYED SYEDISAYLL SKNNAIEPRS FSGGGSQVQL VQSGGGLVQA   780
GDSLRLSCAA SGRTFIRYAM AWFRQAPGKE REFVAAIPQS GGRSYYADSV KGRFTISRDN   840
AKNTVYLQMN SLKPEDTAVY SCAATSTYYG RSAYSSHSGG YDYWGQGTQV TVSSGGGSGG   900
GSGGGSGGGS QVQLVQSGGG LVQAGDSLRL SCAASGRTFI RYAMAWFRQA PGKEREFVAA   960
IPQSGGRSYY ADSVKGRFTI SRDNAKNTVY LQMNSLKPED TAVYSCAATS TYYGRSAYSS  1020
HSGGYDYWGQ GTQVTVSSGG GSEITRTTLQ SDQEEIDYDD TISVEMKKED FDIYDEDENQ  1080
SPRSFQKKTR HYFIAAVERL WDYGMSSSPH VLRNRAQSGS VPQFKKVVFQ EFTDGSFTQP  1140
LYRGELNEHL GLLGPYIRAE VEDNIMVTFR NQASRPYSFY SSLISYEEDQ RQGAEPRKNF  1200
VKPNETKTYF WKVQHHMAPT KDEFDCKAWA YFSDVDLEKD VHSGLIGPLL VCHTNTLNPA  1260
HGRQVTVQEF ALFFTIFDET KSWYFTENME RNCRAPCNIQ MEDPTFKENY RFHAINGYIM  1320
DTLPGLVMAQ DQRIRWYLLS MGSNENIHSI HFSGHVFTVR KKEEYKMALY NLYPGVFETV  1380
EMLPSKAGIW RVECLIGEHL HAGMSTLFLV YSNKCQTPLG MASGHIRDFQ ITASGQYGQW  1440
APKLARLHYS GSINAWSTKE PFSWIKVDLL APMIIHGIKT QGARQKFSSL YISQFIIMYS  1500
LDGKKWQTYR GNSTGTLMVF FGNVDSSGIK HNIFNPPIIA RYIRLHPTHY SIRSTLRMEW  1560
MGCDLNSCSM PLGMESKAIS DAQITASSYF TNMFATWSPS KARLHLQGRS NAWRPQVNNP  1620
KEWLQVDFQK TMKVTGVTTQ GVKSLLTSMY VKEFLISSSQ DGHQWTLFFQ NGKVKVFQGN  1680
QDSFTPVVNS LDPPLLTRYL RIHPQSWVHQ IALRMEVLGC EAQDLY                 1726

SEQ ID NO: 14     moltype = AA  length = 761
FEATURE           Location/Qualifiers
REGION            1..761
                  note = Synthetic FVII-KB13-bv SEQ ID NO: 14
source            1..761
                  mol_type = protein
                  organism = synthetic construct
SEQUENCE: 14
MVSQALRLLC LLLGLQGCLA AGGVAKASGG ETRDMPWKPG PHRVFVTQEE AHGVLHRRRR    60
ANAFLEELRP GSLERECKEE QCSFEEAREI FKDAERTKLF WISYSDGDQC ASSPCQNGGS   120
```

```
CKDQLQSYIC FCLPAFEGRN CETHKDDQLI CVNENGGCEQ YCSDHTGTKR SCRCHEGYSL  180
LADGVSCTPT VEYPCGKIPI LEKRNASKPQ GRIVGGKVCP KGECPQVLLL VNGAQLCGGT  240
LINTIWVVSA AHCFDKIKNW RNLIAVLGEH DLSEHDGDEQ SRRVAQVIIP STYVPGTTNH  300
DIALLRLHQP VVLTDHVVPL CLPERTFSER TLAFVRFSLV SGWGQLLDRG ATALELMVLN  360
VPRLMTQDCL QQSRKVGDSP NITEYMFCAG YSDGSKDSCK GDSGGPHATH YRGTWYLTGI  420
VSWGQGCATV GHFGVYTRVS QYIEWLQKLM RSEPRPGVLL RAPFPLTPRG VRLGGGSGGG  480
SGGGSGGGSQ VQLVQSGGGL VQAGDSLRLS CAASGRTFIR YAMAWFRQAP GKEREFVAAI  540
PQSGGRSYYA DSVKGRFTIS RDNAKNTVYL QMNSLKPEDT AVYSCAATST YYGRSAYSSH  600
SGGYDYWGQG TQVTVSSGGG SGGGSGGGSG GGSQVQLVQS GGGLVQAGDS LRLSCAASGR  660
TFIRYAMAWF RQAPGKEREF VAAIPQSGGR SYYADSVKGR FTISRDNAKN TVYLQMNSLK  720
PEDTAVYSCA ATSTYYGRSA YSSHSGGYDY WGQGTQVTVS S                      761

SEQ ID NO: 15          moltype = AA  length = 12
FEATURE                Location/Qualifiers
REGION                 1..12
                       note = Synthetic SEQ ID NO: 15
source                 1..12
                       mol_type = protein
                       organism = synthetic construct
SEQUENCE: 15
EDQVDPRLID GK                                                      12

SEQ ID NO: 16          moltype = AA  length = 1746
FEATURE                Location/Qualifiers
REGION                 1..1746
                       note = Synthetic FVIII_KB0013bv(6GGGS) SEQ ID NO: 16
source                 1..1746
                       mol_type = protein
                       organism = synthetic construct
SEQUENCE: 16
MQIELSTCFF LCLLRFCFSA TRRYYLGAVE LSWDYMQSDL GELPVDARFP PRVPKSFPFN  60
TSVVYKKTLF VEFTDHLFNI AKPRPPWMGL LGPTIQAEVY DTVVITLKNM ASHPVSLHAV  120
GVSYWKASEG AEYDDQTSQR EKEDDKVFPG GSHTYVWQVL KENGPMASDP LCLTYSYLSH  180
VDLVKDLNSG LIGALLVCRE GSLAKEKTQT LHKFILLFAV FDEGKSWHSE TKNSLMQDRD  240
AASARAWPKM HTVNGYVNRS LPGLIGCHRK SVYWHVIGMG TTPEVHSIFL EGHTFLVRNH  300
RQASLEISPI TFLTAQTLLM DLGQFLLFCH ISSHQHDGME AYVKVDSCPE EPQLRMKNNE  360
EAEDYDDDLT DSEMDVVRFD DDNSPSFIQI RSVAKKHPKT WVHYIAAEEE DWDYAPLVLA  420
PDDRSYKSQY LNNGPQRIGR KYKKVRFMAY TDETFKTREA IQHESGILGP LLYGEVGDTL  480
LIIFKNQASR PYNIYPHGIT DVRPLYSRRL PKGVKHLKDF PILPGEIFKY KWTVTVEDGP  540
TKSDPRCLTR YYSSFVNMER DLASGLIGPL LICYKESVDQ RGNQIMSDKR NVILFSVFDE  600
NRSWYLTENI QRFLPNPAGV QLEDPEFQAS NIMHSINGYV FDSLQLSVCL HEVAYWYILS  660
IGAQTDFLSV FFSGYTFKHK MVYEDTLTLF PFSGETVFMS MENPGLWILG CHNSDFRNRG  720
MTALLKVSSC DKNTGDYYED SYEDISAYLL SKNNAIEPRS FSGGGSQVQL VQSGGGLVQA  780
GDSLRLSCAA SGRTFIRYAM AWFRQAPGKE REFVAAIPQS GGRSYYADSV KGRFTISRDN  840
AKNTVYLQMN SLKPEDTAVY SCAATSTYYG RSAYSSHSGG YDYWGQGTQV TVSSGGGSGG  900
GSGGGSGGGS QVQLVQSGGG LVQAGDSLRL SCAASGRTFI RYAMAWFRQA PGKEREFVAA  960
IPQSGGRSYY ADSVKGRFTI SRDNAKNTVY LQMNSLKPED TAVYSCAATS TYYGRSAYSS  1020
HSGGYDYWGQ GTQVTVSSGG GSGGGSGGGS GGGSGGGSGG GSEITRTTLQ SDQEEIDYDD  1080
TISVEMKKED FDIYDEDENQ SPRSFQKKTR HYFIAAVERL WDYGMSSSPH VLRNRAQSGS  1140
VPQFKKVVFQ EFTDGSFTQP LYRGELNEHL GLLGPYIRAE VEDNIMVTFR NQASRPYSFY  1200
SSLISYEEDQ RQGAEPRKNF VKPNETKTYF WKVQHHMAPT KDEFDCKAWA YFSDVDLEKD  1260
VHSGLIGPLL VCHTNTLNPA HGRQVTVQEF ALFFTIFDET KSWYFTENME RNCRAPCNIQ  1320
MEDPTFKENY RFHAINGYIM DTLPGLVMAQ DQRIRWYLLS MGSNENIHSI HFSGHVFTVR  1380
KKEEYKMALY NLYPGVFETV EMLPSKAGIW RVECLIGEHL HAGMSTLFLV YSNKCQTPLG  1440
MASGHIRDFQ ITASGQYGQW APKLARLHYS GSINAWSTKE PFSWIKVDLL APMIIHGIKT  1500
QGARQKFSSL YISQFIIMYS LDGKKWQTYR GNSTGTLMVF FGNVDSSGIK HNIFNPPIIA  1560
RYIRLHPTHY SIRSTLRMEW MGCDLNSCSM PLGMESKAIS DAQITASSYF TNMFATWSPS  1620
KARLHLQGRS NAWRPQVNNP KEWLQVDFQK TMKVTGVTTQ GVKSLLTSMY VKEFLISSSQ  1680
DGHQWTLFFQ NGKVKVFQGN QDSFTPVVNS LDPPLLTRYL RIHPQSWVHQ IALRMEVLGC  1740
EAQDLY                                                            1746

SEQ ID NO: 17          moltype = AA  length = 1746
FEATURE                Location/Qualifiers
REGION                 1..1746
                       note = Synthetic FVIII_KB0013bv(6GGGS)_Y1680F SEQ ID NO: 17
source                 1..1746
                       mol_type = protein
                       organism = synthetic construct
SEQUENCE: 17
MQIELSTCFF LCLLRFCFSA TRRYYLGAVE LSWDYMQSDL GELPVDARFP PRVPKSFPFN  60
TSVVYKKTLF VEFTDHLFNI AKPRPPWMGL LGPTIQAEVY DTVVITLKNM ASHPVSLHAV  120
GVSYWKASEG AEYDDQTSQR EKEDDKVFPG GSHTYVWQVL KENGPMASDP LCLTYSYLSH  180
VDLVKDLNSG LIGALLVCRE GSLAKEKTQT LHKFILLFAV FDEGKSWHSE TKNSLMQDRD  240
AASARAWPKM HTVNGYVNRS LPGLIGCHRK SVYWHVIGMG TTPEVHSIFL EGHTFLVRNH  300
RQASLEISPI TFLTAQTLLM DLGQFLLFCH ISSHQHDGME AYVKVDSCPE EPQLRMKNNE  360
EAEDYDDDLT DSEMDVVRFD DDNSPSFIQI RSVAKKHPKT WVHYIAAEEE DWDYAPLVLA  420
PDDRSYKSQY LNNGPQRIGR KYKKVRFMAY TDETFKTREA IQHESGILGP LLYGEVGDTL  480
LIIFKNQASR PYNIYPHGIT DVRPLYSRRL PKGVKHLKDF PILPGEIFKY KWTVTVEDGP  540
TKSDPRCLTR YYSSFVNMER DLASGLIGPL LICYKESVDQ RGNQIMSDKR NVILFSVFDE  600
```

-continued

```
NRSWYLTENI QRFLPNPAGV QLEDPEFQAS NIMHSINGYV FDSLQLSVCL HEVAYWYILS  660
IGAQTDFLSV FFSGYTFKHK MVYEDTLTLF PFSGETVFMS MENPGLWILG CHNSDFRNRG  720
MTALLKVSSC DKNTGDYYED SYEDISAYLL SKNNAIEPRS FSGGGSQVQL VQSGGGLVQA  780
GDSLRLSCAA SGRTFIRYAM AWFRQAPGKE REFVAAIPQS GGRSYYADSV KGRFTISRDN  840
AKNTVYLQMN SLKPEDTAVY SCAATSTYYG RSAYSSHSGG YDYWGQGTQV TVSSGGGSGG  900
GSGGGSGGGS QVQLVQSGGG LVQAGDSLRL SCAASGRTFI RYAMAWFRQA PGKEREFVAA  960
IPQSGGRSYY ADSVKGRFTI SRDNAKNTVY LQMNSLKPED TAVYSCAATS TYYGRSAYSS 1020
HSGGYDYWGQ GTQVTVSSGG GSGGGSGGGS GGGSGGGSGG GSEITRTTLQ SDQEEIDYDD 1080
TISVEMKKED FDIFDEDENQ SPRSFQKKTR HYFIAAVERL WDYGMSSSPH VLRNRAQSGS 1140
VPQFKKVVFQ EFTDGSFTQP LYRGELNEHL GLLGPYIRAE VEDNIMVTFR NQASRPYSFY 1200
SSLISYEEDQ RQGAEPRKNF VKPNETKTYF WKVQHHMAPT KDEFDCKAWA YFSDVDLEKD 1260
VHSGLIGPLL VCHTNTLNPA HGRQVTVQEF ALFFTIFDET KSWYFTENME RNCRAPCNIQ 1320
MEDPTFKENY RFHAINGYIM DTLPGLVMAQ DQRIRWYLLS MGSNENIHSI HFSGHVFTVR 1380
KKEEYKMALY NLYPGVFETV EMLPSKAGIW RVECLIGEHL HAGMSTLFLV YSNKCQTPLG 1440
MASGHIRDFQ ITASGQYGQW APKLARLHYS GSINAWSTKE PFSWIKVDLL APMIIHGIKT 1500
QGARQKFSSL YISQFIIMYS LDGKKWQTYR GNSTGTLMVF FGNVDSSGIK HNIFNPPIIA 1560
RYIRLHPTHY SIRSTLRMEW MGCDLNSCSM PLGMESKAIS DAQITASSYF TNMFATWSPS 1620
KARLHLQGRS NAWRPQVNNP KEWLQVDFQK TMKVTGVTTQ GVKSLLTSMY VKEFLISSSQ 1680
DGHQWTLFFQ NGKVKVFQGN QDSFTPVVNS LDPPLLTRYL RIHPQSWVHQ IALRMEVLGC 1740
EAQDLY                                                          1746

SEQ ID NO: 18         moltype = AA   length = 1753
FEATURE               Location/Qualifiers
REGION                1..1753
                      note = Synthetic FVIII_BD_Cter-0013bv SEQ ID NO: 18
source                1..1753
                      mol_type = protein
                      organism = synthetic construct
SEQUENCE: 18
MQIELSTCFF LCLLRFCFSA TRRYYLGAVE LSWDYMQSDL GELPVDARFP PRVPKSFPFN  60
TSVVYKKTLF VEFTDHLFNI AKPRPPWMGL LGPTIQAEVY DTVVITLKNM ASHPVSLHAV  120
GVSYWKASEG AEYDDQTSQR EKEDDKVFPG GSHTYVWQVL KENGPMASDP LCLTYSYLSH  180
VDLVKDLNSG LIGALLVCRE GSLAKEKTQT LHKFILLFAV FDEGKSWHSE TKNSLMQDRD  240
AASARAWPKM HTVNGYVNRS LPGLIGCHRK SVYWHVIAGM TTPEVHSIFL EGHTFLVRNH  300
RQASLEISPI TFLTAQTLLM DLGQFLLFCH ISSHQHDGME AYVKVDSCPE EPQLRMKNNE  360
EAEDYDDDLT DSEMDVVRFD DDNSPSFIQI RSVAKKHPKT WVHYIAAEEE DWDYAPLVLA  420
PDDRSYKSQY LNNGPQRIGR KYKKVRFMAY TDETFKTREA IQHESGILGP LLYGEVGDTL  480
LIIFKNQASR PYNIYPHGIT DVRPLYSRRL PKGVKHLKDF PILPGEIFKY KWTVTVEDGP  540
TKSDPRCLTR YYSSFVNMER DLASGLIGPL LICYKESVDQ RGNQIMSDKR NVILFSVFDE  600
NRSWYLTENI QRFLPNPAGV QLEDPEFQAS NIMHSINGYV FDSLQLSVCL HEVAYWYILS  660
IGAQTDFLSV FFSGYTFKHK MVYEDTLTLF PFSGETVFMS MENPGLWILG CHNSDFRNRG  720
MTALLKVSSC DKNTGDYYED SYEDISAYLL SKNNAIEPRS FSQNPPVLKR HQREITRTTL  780
QSDQEEIDYD DTISVEMKKE DFDIYDEDEN QSPRSFQKKT RHYFIAAVER LWDYGMSSSP  840
HVLRNRAQSG SVPQFKKVVF QEFTDGSFTQ PLYRGELNEH LGLLGPYIRA EVEDNIMVTF  900
RNQASRPYSF YSSLISYEED QRQGAEPRKN FVKPNETKTY FWKVQHHMAP TKDEFDCKAW  960
AYFSDVDLEK DVHSGLIGPL LVCHTNTLNP AHGRQVTVQE FALFFTIFDE TKSWYFTENM 1020
ERNCRAPCNI QMEDPTFKEN YRFHAINGYI MDTLPGLVMA QDQRIRWYLL SMGSNENIHS 1080
IHFSGHVFTV RKKEEYKMAL YNLYPGVFET VEMLPSKAGI WRVECLIGEH LHAGMSTLFL 1140
VYSNKCQTPL GMASGHIRDF QITASGQYGQ WAPKLARLHY SGSINAWSTK EPFSWIKVDL 1200
LAPMIIHGIK TQGARQKFSS LYISQFIIMY SLDGKKWQTY RGNSTGTLMV FFGNVDSSGI 1260
KHNIFNPPII ARYIRLHPTH YSIRSTLRME WMGCDLNSCS MPLGMESKAI SDAQITASSY 1320
FTNMFATWSP SKARLHLQGR SNAWRPQVNN PKEWLQVDFQ KTMKVTGVTT QGVKSLLTSM 1380
YVKEFLISSS QDGHQWTLFF QNGKVKVFQG NQDSFTPVVN SLDPPLLTRY LRIHPQSWVH 1440
QIALRMEVLG CEAQDLYLTP RGVRLGGGSG GGSGGGSGGG SQVQLVQSGG GLVQAGDSLR 1500
LSCAASGRTF IRYAMAWFRQ APGKEREFVA AIPQSGGRSY YADSVKGRFT ISRDNAKNTV 1560
YLQMNSLKPE DTAVYSCAAT STYYGRSAYS SHSGGYDYWG QGTQVTVSSG GGSGGGSGGG 1620
SGGGSQVQLV QSGGGLVQAG DSLRLSCAAS GRTFIRYAMA WFRQAPGKER EFVAAIPQSG 1680
GRSYYADSVK GRFTISRDNA KNTVYLQMNS LKPEDTAVYS CAATSTYYGR SAYSSHSGGY 1740
DYWGQGTQVT VSS                                                   1753

SEQ ID NO: 19         moltype = AA   length = 1753
FEATURE               Location/Qualifiers
REGION                1..1753
                      note = Synthetic FVIII_BD_Cter-0013bv_Y1680F SEQ ID NO: 19
source                1..1753
                      mol_type = protein
                      organism = synthetic construct
SEQUENCE: 19
MQIELSTCFF LCLLRFCFSA TRRYYLGAVE LSWDYMQSDL GELPVDARFP PRVPKSFPFN  60
TSVVYKKTLF VEFTDHLFNI AKPRPPWMGL LGPTIQAEVY DTVVITLKNM ASHPVSLHAV  120
GVSYWKASEG AEYDDQTSQR EKEDDKVFPG GSHTYVWQVL KENGPMASDP LCLTYSYLSH  180
VDLVKDLNSG LIGALLVCRE GSLAKEKTQT LHKFILLFAV FDEGKSWHSE TKNSLMQDRD  240
AASARAWPKM HTVNGYVNRS LPGLIGCHRK SVYWHVIGMD TTPEVHSIFL EGHTFLVRNH  300
RQASLEISPI TFLTAQTLLM DLGQFLLFCH ISSHQHDGME AYVKVDSCPE EPQLRMKNNE  360
EAEDYDDDLT DSEMDVVRFD DDNSPSFIQI RSVAKKHPKT WVHYIAAEEE DWDYAPLVLA  420
PDDRSYKSQY LNNGPQRIGR KYKKVRFMAY TDETFKTREA IQHESGILGP LLYGEVGDTL  480
LIIFKNQASR PYNIYPHGIT DVRPLYSRRL PKGVKHLKDF PILPGEIFKY KWTVTVEDGP  540
TKSDPRCLTR YYSSFVNMER DLASGLIGPL LICYKESVDQ RGNQIMSDKR NVILFSVFDE  600
NRSWYLTENI QRFLPNPAGV QLEDPEFQAS NIMHSINGYV FDSLQLSVCL HEVAYWYILS  660
```

```
IGAQTDFLSV FFSGYTFKHK MVYEDTLTLF PFSGETVFMS MENPGLWILG CHNSDFRNRG   720
MTALLKVSSC DKNTGDYYED SYEDISAYLL SKNNAIEPRS FSQNPPVLKR HQREITRTTL   780
QSDQEEIDYD DTISVEMKKE DFDIFDEDEN QSPRSFQKKT RHYFIAAVER LWDYGMSSSP   840
HVLRNRAQSG SVPQFKKVVF QEFTDGSFTQ PLYRGELNEH LGLLGPYIRA EVEDNIMVTF   900
RNQASRPYSF YSSLISYEED QRQGAEPRKN FVKPNETKTY FWKVQHHMAP TKDEFDCKAW   960
AYFSDVDLEK DVHSGLIGPL LVCHTNTLNP AHGRQVTVQE FALFFTIFDE TKSWYFTENM  1020
ERNCRAPCNI QMEDPTFKEN YRFHAINGYI MDTLPGLVMA QDQRIRWYLL SMGSNENIHS  1080
IHFSGHVFTV RKKEEYKMAL YNLYPGVFET VEMLPSKAGI WRVECLIGEH LHAGMSTLFL  1140
VYSNKCQTPL GMASGHIRDF QITASGQYGQ WAPKLARLHY SGSINAWSTK EPFSWIKVDL  1200
LAPMIIHGIK TQGARQKFSS LYISQFIIMY SLDGKKWQTY RGNSTGTLMV FFGNVDSSGI  1260
KHNIFNPPII ARYIRLHPTH YSIRSTLRME WMGCDLNSCS MPLGMESKAI SDAQITASSY  1320
FTNMFATWSP SKARLHLQGR SNAWRPQVNN PKEWLQVDFQ KTMKVTGVTT QGVKSLLTSM  1380
YVKEFLISSS QDGHQWTLFF QNGKVKVFQG NQDSFTPVVN SLDPPLLTRY LRIHPQSWVH  1440
QIALRMEVLG CEAQDLYLTP RGVRLGGGSG GGSGGGSGGG SQVQLVQSGG GLVQAGDSLR  1500
LSCAASGRTF IRYAMAWFRQ APGKEREFVA AIPQSGGRSY YADSVKGRFT ISRDNAKNTV  1560
YLQMNSLKPE DTAVYSCAAT STYYGRSAYS SHSGGYDYWG QGTQVTVSSG GGSGGGSGGG  1620
SGGGSQVQLV QSGGGLVQAG DSLRLSCAAS GRTFIRYAMA WFRQAPGKER EFVAAIPQSG  1680
GRSYYADSVK GRFTISRDNA KNTVYLQMNS LKPEDTAVYS CAATSTYYGR SAYSSHSGGY  1740
DYWGQGTQVT VSS                                                     1753

SEQ ID NO: 20          moltype = AA  length = 2022
FEATURE                Location/Qualifiers
REGION                 1..2022
                       note = Synthetic FVIII_KB0013bv_Cter-0013bv SEQ ID NO: 20
source                 1..2022
                       mol_type = protein
                       organism = synthetic construct
SEQUENCE: 20
MQIELSTCFF LCLLRFCFSA TRRYYLGAVE LSWDYMQSDL GELPVDARFP PRVPKSFPFN   60
TSVVYKKTLF VEFTDHLFNI AKPRPPWMGL LGPTIQAEVY DTVVITLKNM ASHPVSLHAV  120
GVSYWKASEG AEYDDQTSQR EKEDDKVFPG GSHTYVWQVL KENGPMASDP LCLTYSYLSH  180
VDLVKDLNSG LIGALLVCRE GSLAKEKTQT LHKFILLFAV FDEGKSWHSE TKNSLMQDRD  240
AASARAWPKM HTVNGYVNRS LPGLIGCHRK SVYWHVIGMG TTPEVHSIFL EGHTFLVRNH  300
RQASLEISPI TFLTAQTLLM DLGQFLLFCH ISSHQHDGME AYVKVDSCPE EPQLRMKNNE  360
EAEDYDDDLT DSEMDVVRFD DDNSPSFIQI RSVAKKHPKT WVHYIAAEEE DWDYAPLVLA  420
PDDRSYKSQY LNNGPQRIGR KYKKVRFMAY TDETFKTREA IQHESGILGP LLYGEVGDTL  480
LIIFKNQASR PYNIYPHGIT DVRPLYSRRL PKGVKHLKDF PILPGEIFKY KWTVTVEDGP  540
TKSDPRCLTR YYSSFVNMER DLASGLIGPL LICYKESVDQ RGNQIMSDKR NVILFSVFDE  600
NRSWYLTENI QRFLPNPAGV QLEDPEFQAS NIMHSINGYV FDSLQLSVCL HEVAYWYILS  660
IGAQTDFLSV FFSGYTFKHK MVYEDTLTLF PFSGETVFMS MENPGLWILG CHNSDFRNRG   720
MTALLKVSSC DKNTGDYYED SYEDISAYLL SKNNAIEPRS FSGGGSQVQL VQSGGGLVQA   780
GDSLRLSCAA SGRTFIRYAM AWFRQAPGKE REFVAAIPQS GGRSYYADSV KGRFTISRDN   840
AKNTVYLQMN SLKPEDTAVY SCAATSTYYG RSAYSSHSGG YDYWGQGTQV TVSSGGGSGG   900
GSGGGSGGGS QVQLVQSGGG LVQAGDSLRL SCAASGRTFI RYAMAWFRQA PGKEREFVAA   960
IPQSGGRSYY ADSVKGRFTI SRDNAKNTVY LQMNSLKPED TAVYSCAATS TYYGRSAYSS  1020
HSGGYDYWGQ GTQVTVSSGG GSEITRTTLQ SDQEEIDYDD TISVEMKKED FDIYDEDENQ  1080
SPRSFQKKTR HYFIAAVERL WDYGMSSSPH VLRNRAQSGS VPQFKKVVFQ EFTDGSFTQP  1140
LYRGELNEHL GLLGPYIRAE VEDNIMVTFR NQASRPYSFY SSLISYEEDQ RQGAEPRKNF  1200
VKPNETKTYF WKVQHMAPT KDEFDCKAWA YFSDVDLEKD VHSGLIGPLL VCHTNTLNPA  1260
HGRQVTVQEF ALFFTIFDET KSWYFTENME RNCRAPCNIQ MEDPTFKENY RFHAINGYIM  1320
DTLPGLVMAQ DQRIRWYLLS MGSNENIHSI HFSGHVFTVR KKEEYKMALY NLYPGVFETV  1380
EMLPSKAGIW RVECLIGEHL HAGMSTLFLV YSNKCQTPLG MASGHIRDFQ ITASGQYGQW  1440
APKLARLHYS GSINAWSTKE PFSWIKVDLL APMIIHGIKT QGARQKFSSL YISQFIIMYS  1500
LDGKKWQTYG NSTGTLMVF FGNVDSSGIK HNIFNPPIIA RYIRLHPTHY SIRSTLRMEW  1560
MGCDLNSCSM PLGMESKAIS DAQITASSYF TNMFATWSPS KARLHLQGRS NAWRPQVNN  1620
KEWLQVDFQK TMKVTGVTTQ GVKSLLTSMY VKEFLISSSQ DGHQWTLFFQ NGKVKVFQGN  1680
QDSFTPVVNS LDPPLLTRYL RIHPQSWVHQ IALRMEVLGC EAQDLYLTPR GVRLGGGSGG  1740
GSGGGSGGGS QVQLVQSGGG LVQAGDSLRL SCAASGRTFI RYAMAWFRQA PGKEREFVAA  1800
IPQSGGRSYY ADSVKGRFTI SRDNAKNTVY LQMNSLKPED TAVYSCAATS TYYGRSAYSS  1860
HSGGYDYWGQ GTQVTVSSGG GSGGGSGGGS GGGSQVQLVQ SGGGLVQAGD SLRLSCAASG  1920
RTFIRYAMAW FRQAPGKERE FVAAIPQSGG RSYYADSVKG RFTISRDNAK NTVYLQMNSL  1980
KPEDTAVYSC AATSTYYGRS AYSSHSGGYD YWGQGTQVTV SS                     2022

SEQ ID NO: 21          moltype = AA  length = 2022
FEATURE                Location/Qualifiers
REGION                 1..2022
                       note = SyntheticFVIII_KB0013bv_Cter-0013bv_Y1680F SEQ ID
                       NO: 21
source                 1..2022
                       mol_type = protein
                       organism = synthetic construct
SEQUENCE: 21
MQIELSTCFF LCLLRFCFSA TRRYYLGAVE LSWDYMQSDL GELPVDARFP PRVPKSFPFN   60
TSVVYKKTLF VEFTDHLFNI AKPRPPWMGL LGPTIQAEVY DTVVITLKNM ASHPVSLHAV  120
GVSYWKASEG AEYDDQTSQR EKEDDKVFPG GSHTYVWQVL KENGPMASDP LCLTYSYLSH  180
VDLVKDLNSG LIGALLVCRE GSLAKEKTQT LHKFILLFAV FDEGKSWHSE TKNSLMQDRD  240
AASARAWPKM HTVNGYVNRS LPGLIGCHRK SVYWHVIGMG TTPEVHSIFL EGHTFLVRNH  300
RQASLEISPI TFLTAQTLLM DLGQFLLFCH ISSHQHDGME AYVKVDSCPE EPQLRMKNNE  360
EAEDYDDDLT DSEMDVVRFD DDNSPSFIQI RSVAKKHPKT WVHYIAAEEE DWDYAPLVLA  420
```

```
PDDRSYKSQY LNNGPQRIGR KYKKVRFMAY TDETFKTREA IQHESGILGP LLYGEVGDTL  480
LIIFKNQASR PYNIYPHGIT DVRPLYSRRL PKGVKHLKDF PILPGEIFKY KWTVTVEDGP  540
TKSDPRCLTR YYSSFVNMER DLASGLIGPL LICYKESVDQ RGNQIMSDKR NVILFSVFDE  600
NRSWYLTENI QRFLPNPAGV QLEDPEFQAS NIMHSINGYV FDSLQLSVCL HEVAYWYILS  660
IGAQTDFLSV FFSGYTFKHK MVYEDTLTLF PFSGETVFMS MENPGLWILG CHNSDFRNRG  720
MTALLKVSSC DKNTGDYYED SYEDISAYLL SKNNAIEPRS FSGGGSQVQL VQSGGGLVQA  780
GDSLRLSCAA SGRTFIRYAM AWFRQAPGKE REFVAAIPQS GGRSYYADSV KGRFTISRDN  840
AKNTVYLQMN SLKPEDTAVY SCAATSTYYG RSAYSSHSGG YDYWGQGTQV TVSSGGGSGG  900
GSGGGSGGGS QVQLVQSGGG LVQAGDSLRL SCAASGRTFI RYAMAWFRQA PGKEREFVAA  960
IPQSGGRSYY ADSVKGRFTI SRDNAKNTVY LQMNSLKPED TAVYSCAATS TYYGRSAYSS  1020
HSGGYDYWGQ GTQVTVSSGG GSEITRTTLQ SDQEEIDYDD TISVEMKKED FDIFDEDENQ  1080
SPRSFQKKTR HYFIAAVERL WDYGMSSSPH VLRNRAQSGS VPQFKKVVFQ EFTDGSFTQP  1140
LYRGELNEHL GLLGPYIRAE VEDNIMVTFR NQASRPYSFY SSLISYEEDQ RQGAEPRKNF  1200
VKPNETKTYF WKVQHHMAPT KDEFDCKAWA YFSDVDLEKD VHSGLIGPLL VCHTNTLNPA  1260
HGRQVTVQEF ALFFTIFDET KSWYFTENME RNCRAPCNIQ MEDPTFKENY RFHAINGYIM  1320
DTLPGLVMAQ DQRIRWYLLS MGSNENIHSI HFSGHVFTVR KKEEYKMALY NLYPGVFETV  1380
EMLPSKAGIW RVECLIGEHL HAGMSTLFLV YSNKCQTPLG MASGHIRDFQ ITASGQYGQW  1440
APKLARLHYS GSINAWSTKE PFSWIKVDLL APMIIHGIKT QGARQKFSSL YISQFIIMYS  1500
LDGKKWQTYR GNSTGTLMVF FGNVDSSGIK HNIFNPPIIA RYIRLHPTHY SIRSTLRMEW  1560
MGCDLNSCSM PLGMESKAIS DAQITASSYF TNMFATWSPS KARLHLQGRS NAWRPQVNNP  1620
KEWLQVDFQK TMKVTGVTTQ GVKSLLTSMY VKEFLISSSQ DGHQWTLFFQ NGKVKVFQGN  1680
QDSFTPVVNS LDPPLLTRYL RIHPQSWVHQ IALRMEVLGC EAQDLYLTPR GVRLGGGSGG  1740
GSGGGSGGGS QVQLVQSGGG LVQAGDSLRL SCAASGRTFI RYAMAWFRQA PGKEREFVAA  1800
IPQSGGRSYY ADSVKGRFTI SRDNAKNTVY LQMNSLKPED TAVYSCAATS TYYGRSAYSS  1860
HSGGYDYWGQ GTQVTVSSGG GSGGGSGGGS GGGSQVQLVQ SGGGLVQAGD SLRLSCAASG  1920
RTFIRYAMAW FRQAPGKERE FVAAIPQSGG RSYYADSVKG RFTISRDNAK NTVYLQMNSL  1980
KPEDTAVYSC AATSTYYGRS AYSSHSGGYD YWGQGTQVTV SS                    2022
```

```
SEQ ID NO: 22          moltype = AA  length = 2042
FEATURE                Location/Qualifiers
REGION                 1..2042
                       note = Synthetic FVIII_KB0013bv(6GGGS)_Cter-0013bv SEQ ID
                       NO: 22
source                 1..2042
                       mol_type = protein
                       organism = synthetic construct
SEQUENCE: 22
MQIELSTCFF LCLLRFCFSA TRRYYLGAVE LSWDYMQSDL GELPVDARFP PRVPKSFPFN  60
TSVVYKKTLF VEFTDHLFNI AKPRPPWMGL LGPTIQAEVY DTVVITLKNM ASHPVSLHAV  120
GVSYWKASEG AEYDDQTSQR EKEDDKVFPG GSHTYVWQVL KENGPMASDP LCLTYSYLSH  180
VDLVKDLNSG LIGALLVCRE GSLAKEKTQT LHKFILLFAV FDEGKSWHSE TKNSLMQDRD  240
AASARAWPKM HTVNGYVNRS LPGLIGCHRK SVYWHVIGMG TTPEVHSIFL EGHTFLVRNH  300
RQASLEISPI TFLTAQTLLM DLGQFLLFCH ISSHQHDGME AYVKVDSCPE EPQLRMKNNE  360
EAEDYDDDLT DSEMDVVRFD DDNSPSFIQI RSVAKKHPKT WVHYIAAEEE DWDYAPLVLA  420
PDDRSYKSQY LNNGPQRIGR KYKKVRFMAY TDETFKTREA IQHESGILGP LLYGEVGDTL  480
LIIFKNQASR PYNIYPHGIT DVRPLYSRRL PKGVKHLKDF PILPGEIFKY KWTVTVEDGP  540
TKSDPRCLTR YYSSFVNMER DLASGLIGPL LICYKESVDQ RGNQIMSDKR NVILFSVFDE  600
NRSWYLTENI QRFLPNPAGV QLEDPEFQAS NIMHSINGYV FDSLQLSVCL HEVAYWYILS  660
IGAQTDFLSV FFSGYTFKHK MVYEDTLTLF PFSGETVFMS MENPGLWILG CHNSDFRNRG  720
MTALLKVSSC DKNTGDYYED SYEDISAYLL SKNNAIEPRS FSGGGSQVQL VQSGGGLVQA  780
GDSLRLSCAA SGRTFIRYAM AWFRQAPGKE REFVAAIPQS GGRSYYADSV KGRFTISRDN  840
AKNTVYLQMN SLKPEDTAVY SCAATSTYYG RSAYSSHSGG YDYWGQGTQV TVSSGGGSGG  900
GSGGGSGGGS QVQLVQSGGG LVQAGDSLRL SCAASGRTFI RYAMAWFRQA PGKEREFVAA  960
IPQSGGRSYY ADSVKGRFTI SRDNAKNTVY LQMNSLKPED TAVYSCAATS TYYGRSAYSS  1020
HSGGYDYWGQ GTQVTVSSGG GSGGGSGGGS GGGSGGGSGG GSEITRTTLQ SDQEEIDYDD  1080
TISVEMKKED FDIYDEDENQ SPRSFQKKTR HYFIAAVERL WDYGMSSSPH VLRNRAQSGS  1140
VPQFKKVVFQ EFTDGSFTQP LYRGELNEHL GLLGPYIRAE VEDNIMVTFR NQASRPYSFY  1200
SSLISYEEDQ RQGAEPRKNF VKPNETKTYF WKVQHHMAPT KDEFDCKAWA YFSDVDLEKD  1260
VHSGLIGPLL VCHTNTLNPA HGRQVTVQEF ALFFTIFDET KSWYFTENME RNCRAPCNIQ  1320
MEDPTFKENY RFHAINGYIM DTLPGLVMAQ DQRIRWYLLS MGSNENIHSI HFSGHVFTVR  1380
KKEEYKMALY NLYPGVFETV EMLPSKAGIW RVECLIGEHL HAGMSTLFLV YSNKCQTPLG  1440
MASGHIRDFQ ITASGQYGQW APKLARLHYS GSINAWSTKE PFSWIKVDLL APMIIHGIKT  1500
QGARQKFSSL YISQFIIMYS LDGKKWQTYR GNSTGTLMVF FGNVDSSGIK HNIFNPPIIA  1560
RYIRLHPTHY SIRSTLRMEW MGCDLNSCSM PLGMESKAIS DAQITASSYF TNMFATWSPS  1620
KARLHLQGRS NAWRPQVNNP KEWLQVDFQK TMKVTGVTTQ GVKSLLTSMY VKEFLISSSQ  1680
DGHQWTLFFQ NGKVKVFQGN QDSFTPVVNS LDPPLLTRYL RIHPQSWVHQ IALRMEVLGC  1740
EAQDLYLTPR GVRLGGGSGG GSGGGSGGGS QVQLVQSGGG LVQAGDSLRL SCAASGRTFI  1800
RYAMAWFRQA PGKEREFVAA IPQSGGRSYY ADSVKGRFTI SRDNAKNTVY LQMNSLKPED  1860
TAVYSCAATS TYYGRSAYSS HSGGYDYWGQ GTQVTVSSGG GSGGGSGGGS GGGSQVQLVQ  1920
SGGGLVQAGD SLRLSCAASG RTFIRYAMAW FRQAPGKERE FVAAIPQSGG RSYYADSVKG  1980
RFTISRDNAK NTVYLQMNSL KPEDTAVYSC AATSTYYGRS AYSSHSGGYD YWGQGTQVTV  2040
SS                                                               2042
```

```
SEQ ID NO: 23          moltype = AA  length = 2042
FEATURE                Location/Qualifiers
REGION                 1..2042
                       note = Synthetic FVIII_KB0013bv(6GGGS)_Cter-0013bv_Y1680F
                       SEQ ID NO: 23
source                 1..2042
```

-continued

```
                    mol_type = protein
                    organism = synthetic construct
SEQUENCE: 23
MQIELSTCFF  LCLLRFCFSA  TRRYYLGAVE  LSWDYMQSDL  GELPVDARFP  PRVPKSFPFN    60
TSVVYKKTLF  VEFTDHLFNI  AKPRPPWMGL  LGPTIQAEVY  DTVVITLKNM  ASHPVSLHAV   120
GVSYWKASEG  AEYDDQTSQR  EKEDDKVFPG  GSHTYVWQVL  KENGPMASDP  LCLTYSYLSH   180
VDLVKDLNSG  LIGALLVCRE  GSLAKEKTQT  LHKFILLFAV  FDEGKSWHSE  TKNSLMQDRD   240
AASARAWPKM  HTVNGYVNRS  LPGLIGCHRK  SVYWHVIGMG  TTPEVHSIFL  EGHTFLVRNH   300
RQASLEISPI  TFLTAQTLLM  DLGQFLLFCH  ISSHQHDGME  AYVKVDSCPE  EPQLRMKNNE   360
EAEDYDDDLT  DSEMDVVRFD  DDNSPSFIQI  RSVAKKHPKT  WVHYIAAEEE  DWDYAPLVLA   420
PDDRSYKSQY  LNNGPQRIGR  KYKKVRFMAY  TDETFKTREA  IQHESGILGP  LLYGEVGDTL   480
LIIFKNQASR  PYNIYPHGIT  DVRPLYSRRL  PKGVKHLKDF  PILPGEIFKY  KWTVTVEDGP   540
TKSDPRCLTR  YYSSFVNMER  DLASGLIGPL  LICYKESVDQ  RGNQIMSDKR  NVILFSVFDE   600
NRSWYLTENI  QRFLPNPAGV  QLEDPEFQAS  NIMHSINGYV  FDSLQLSVCL  HEVAYWYILS   660
IGAQTDFLSV  FFSGYTFKHK  MVYEDTLTLF  PFSGETVFMS  MENPGLWILG  CHNSDFRNRG   720
MTALLKVSSC  DKNTGDYYED  SYEDISAYLL  SKNNAIEPRS  FSGGGSQVQL  VQSGGGLVQA   780
GDSLRLSCAA  SGRTFIRYAM  AWFRQAPGKE  REFVAAIPQS  GGRSYYADSV  KGRFTISRDN   840
AKNTVYLQMN  SLKPEDTAVY  SCAATSTYYG  RSAYSSHSGG  YDYWGQGTQV  TVSSGGGSGG   900
GSGGGSGGGS  QVQLVQSGGG  LVQAGDSLRL  SCAASGRTFI  RYAMAWFRQA  PGKEREFVAA   960
IPQSGGRSYY  ADSVKGRFTI  SRDNAKNTVY  LQMNSLKPED  TAVYSCAATS  TYYGRSAYSS  1020
HSGGYDYWGQ  GTQVTVSSGG  GSGGGSGGGS  GGGSGGGSGG  GSEITRTTLQ  SDQEEIDYDD  1080
TISVEMKKED  FDIFDEDENQ  SPRSFQKKTR  HYFIAAVERL  WDYGMSSSPH  VLRNRAQSGS  1140
VPQFKKVVFQ  EFTDGSFTQP  LYRGELNEHL  GLLGPYIRAE  VEDNIMVTFR  NQASRPYSFY  1200
SSLISYEEDQ  RQGAEPRKNF  VKPNETKTYF  WKVQHHMAPT  KDEFDCKAWA  YFSDVDLEKD  1260
VHSGLIGPLL  VCHTNTLNPA  HGRQVTVQEF  ALFFTIFDET  KSWYFTENME  RNCRAPCNIQ  1320
MEDPTFKENY  RFHAINGYIM  DTLPGLVMAQ  DQRIRWYLLS  MGSNENIHSI  HFSGHVFTVR  1380
KKEEYKMALY  NLYPGVFETV  EMLPSKAGIW  RVECLIGEHL  HAGMSTLFLV  YSNKCQTPLG  1440
MASGHIRDFQ  ITASGQYGQW  APKLARLHYS  GSINAWSTKE  PFSWIKVDLL  APMIIHGIKT  1500
QGARQKFSSL  YISQFIIMYS  LDGKKWQTYR  GNSTGTLMVF  FGNVDSSGIK  HNIFNPPIIA  1560
RYIRLHPTHY  SIRSTLRMEW  MGCDLNSCSM  PLGMESKAIS  DAQITASSYF  TNMFATWSPS  1620
KARLHLQGRS  NAWRPQVNNP  KEWLQVDFQK  TMKVTGVTTQ  GVKSLLTSMY  VKEFLISSSQ  1680
DGHQWTLFFQ  NGKVKVFQGN  QDSFTPVVNS  LDPPLLTRYL  RIHPQSWVHQ  IALRMEVLGC  1740
EAQDLYLTPR  GVRLGGGSGG  GSGGGSGGGS  QVQLVQSGGG  LVQAGDSLRL  SCAASGRTFI  1800
RYAMAWFRQA  PGKEREFVAA  IPQSGGRSYY  ADSVKGRFTI  SRDNAKNTVY  LQMNSLKPED  1860
TAVYSCAATS  TYYGRSAYSS  HSGGYDYWGQ  GTQVTVSSGG  GSGGGSGGGS  GGGSQVQLVQ  1920
SGGGLVQAGD  SLRLSCAASG  RTFIRYAMAW  FRQAPGKERE  FVAAIPQSGG  RSYYADSVKG  1980
RFTISRDNAK  NTVYLQMNSL  KPEDTAVYSC  AATSTYYGRS  AYSSHSGGYD  YWGQGTQVTV  2040
SS                                                                    2042
```

The invention claimed is:

1. A method of preventing or treating a bleeding disorder in a subject, comprising administering to the subject a therapeutically effective amount of a chimeric polypeptide comprising:
   a) a first polypeptide that is a single-domain antibody (sdAb) directed against von Willebrand Factor (VWF) D'D3 domain, wherein the sdAb comprises SEQ ID NOs: 1, 2 and 3; and
   b) a second polypeptide, wherein said second polypeptide comprises a clotting factor or a binding site directed against a clotting factor.

2. The method of claim 1, wherein the sdAb comprises SEQ ID NO: 4.

3. The method of claim 1, wherein the bleeding disorder is hemophilia A, hemophilia B, or deficiencies or structural abnormalities in fibrinogen, prothrombin, Factor V, Factor VII or Factor X.

4. The method of claim 1, wherein the bleeding disorder is von Willebrand disease.

5. The method of claim 1, wherein the chimeric polypeptide is a bispecific polypeptide.

6. The method of claim 1, wherein the second polypeptide comprises another single-domain antibody.

7. The method of claim 1, wherein the second polypeptide comprises an Fc portion of an antibody.

8. The method of claim 1, wherein the single-domain antibody directed against von Willebrand Factor (VWF) D'D3 domain is fused at the N terminal end of the chimeric polypeptide.

9. The method of claim 1, wherein the single-domain antibody directed against von Willebrand Factor (VWF) D'D3 domain is fused at the C terminal end of the chimeric polypeptide.

10. The method of claim 1, wherein the chimeric polypeptide is administered as part of a pharmaceutical composition comprising the chimeric polypeptide and a pharmaceutically acceptable carrier.

* * * * *